(12) United States Patent
McDonald et al.

(10) Patent No.: US 10,709,859 B2
(45) Date of Patent: Jul. 14, 2020

(54) PATIENT GAS DELIVERY MASK WITH IMPROVED GAS FLOW DISRUPTER

(71) Applicant: SOUTHMEDIC INCORPORATED, Barrie (CA)

(72) Inventors: Lisette McDonald, Barrie (CA); Maurice Lavimodiere, Barrie (CA); Sandy McDonald, Barrie (CA); Alex McDonald, Barrie (CA); Robert Burke, Barrie (CA); Andrew Morum, Barrie (CA); Julius Hajgato, Barrie (CA)

(73) Assignee: SOUTHMEDIC INCORPORATED, Barrie, Ontario (CA)

(*) Notice: Subject to any disclaimer, the term of this patent is extended or adjusted under 35 U.S.C. 154(b) by 0 days.

(21) Appl. No.: 16/599,333

(22) Filed: Oct. 11, 2019

(65) Prior Publication Data

US 2020/0171258 A1 Jun. 4, 2020

Related U.S. Application Data

(60) Provisional application No. 62/774,610, filed on Dec. 3, 2018.

(30) Foreign Application Priority Data

Feb. 19, 2019 (CA) ...................... 3034142

(51) Int. Cl.
*A61M 16/06* (2006.01)
*A61M 16/08* (2006.01)

(52) U.S. Cl.
CPC ........ *A61M 16/06* (2013.01); *A61M 16/0816* (2013.01); *A61M 2202/0208* (2013.01); *A61M 2205/3331* (2013.01); *A61M 2206/14* (2013.01)

(58) Field of Classification Search
CPC .. A61M 16/00; A61M 16/06; A61M 16/0816; A61M 16/085; A61M 2202/0208; A61M 2206/14; A62B 18/02; A61B 5/08; A61B 5/082
See application file for complete search history.

(56) References Cited

U.S. PATENT DOCUMENTS

| | | | |
|---|---|---|---|
| 7,934,501 B2 | 5/2011 | Fu et al. | |
| 8,042,540 B2 | 10/2011 | McDonald et al. | |
| 9,199,052 B2 | 12/2015 | Rubin | |
| 2011/0094513 A1* | 4/2011 | Takatori | A61M 16/06 128/205.25 |

(Continued)

*Primary Examiner* — Joseph D. Boecker
(74) *Attorney, Agent, or Firm* — Pearne & Gordon LLP

(57) ABSTRACT

We disclose a mask for administering a breathable gas to a patient, which comprises a mask body and a gas flow disrupter joined to the mask body for generating a turbulent gas plume rearwardly towards the nose and mouth of the patient. The mask body is configured to position the flow disrupter so as to be spaced from and opposing the patient's nose and mouth region when the mask is worn by the patient. The mask includes a gas inlet for admitting gas from an external source into the mask interior, through the gas flow disrupter. The gas flow disrupter can be configured to generate a turbulent gas plume wherein the velocity of gas exiting the disrupter is approximately the same as the gas velocity entering the mask from the gas inlet.

21 Claims, 28 Drawing Sheets

(56) References Cited

U.S. PATENT DOCUMENTS

| | | | |
|---|---|---|---|
| 2013/0186406 A1* | 7/2013 | Hajgato | A61M 16/06 128/206.28 |
| 2016/0074610 A1* | 3/2016 | Rubin | A61M 16/06 |
| 2017/0095633 A1* | 4/2017 | Falligant | A61M 16/0875 |
| 2019/0255274 A1* | 8/2019 | McDonald | A61M 16/06 |

* cited by examiner

PATIENT GAS DELIVERY MASK WITH IMPROVED GAS FLOW DISRUPTER

FIELD

The invention relates to medical devices for the delivery of a breathable gas to a patient, namely a facial mask having a gas inlet for delivering a gas such as oxygen to the nose and/or mouth of the patient.

BACKGROUND

Gas delivery masks are widely used for medical purposes to deliver oxygen and other breathable gases to a patient. Typically, a conventional mask is configured to substantially cover the nose and mouth region of a patient. A conventional mask includes an inlet for connection with a source of pressurized gas. The mask may also include a baffle, diffuser or other structure to generate a gas plume within the interior of the mask or otherwise control the gas flow properties.

Gas delivery masks are described in the following references:
U.S. Pat. No. 7,934,501
U.S. Pat. No. 8,042,540
U.S. Pat. No. 9,199,052
US 2013/0186406
USA 2017/0095633

Gas delivery masks for medical use face competing requirements. On the one hand, the mask must be able to deliver oxygen or other gas at a relatively high concentration to the patient. Normally, this requires a relatively high flow rate of gas. However, on the other hand, the mask should be comfortable to the user, which generally is improved by a lower rate of gas flow; as well, a lower gas flow rate is more economical to the hospital. As such, it is desirable to improve the efficiency of gas delivery in a mask in order to improve patient comfort and reduce the gas flow rate required to deliver a given gas concentration to the patient. Reduction in gas flow rate also tends to reduce the noise generated by the device.

SUMMARY

We disclose a mask for administering a breathable gas to a patient, which comprises a mask body and a gas flow disrupter joined to the mask body for generating a turbulent gas plume rearwardly towards the nose and mouth of the patient. The mask body is configured to position the flow disrupter so as to be spaced from and opposing the patient's nose and mouth region when the mask is worn by the patient. The mask includes a gas inlet for admitting gas from an external source into the mask interior, through the flow disrupter. Optionally, the mask body includes a manifold region upstream of the flow disrupter. The gas flow disrupter comprises:
- a peripheral wall that defines an interior space within the periphery of the wall, the wall having an inside surface facing the interior space and an outside surface;
- a baffle structure located within the interior space, the baffle structure comprising a baffle member configured to block a portion of the interior space within the gas flow disrupter, the baffle structure further comprising at least one gas turbulence generator consisting of one or more of a rib, a fin, a dimple, a protuberance; and
- at least one gap between the baffle member and the inside surface of the peripheral wall for gas flow through the vortex generator.

In at least some aspects, the gas flow disrupter is configured to generate a turbulent gas plume wherein the velocity of gas exiting the disrupter is approximately the same as the gas velocity entering the mask from the gas inlet.

In one aspect, the baffle member comprises a dome, which in one embodiment has a concave face that faces the inlet, in the path of the gas flow, and optionally, the opposing face consists that faces towards the user is convex.

In some embodiments, the gas turbulence generator(s) extend at least partially into or across the gap between the baffle member and the peripheral wall of the flow disrupter.

We disclose various embodiments of the gas turbulence generator, including at least one fin that is aligned with an axis that is angled relative to the direction of airflow through the flow disrupter, and wherein at least one fin spans the gap between the baffle member and the peripheral wall. The gas turbulence generator may comprise an array of fins that radiate outwardly from the baffle member, within a plane that is generally perpendicular to the gas flow direction, i.e., the fins are aligned with a generally vertical plane. At least one of the fins can be angled relative to a radius of the baffle member. The fins may be arranged in a configuration comprising one or more of parallel pair fins, converging paired fins or equally spaced fins.

Other gas turbulence generators can be provided on an inside surface of the peripheral wall, for example at least one protuberance that extends inwardly towards the baffle structure leaving a gap between the protuberance(s) and the baffle structure. Furthermore, one or more surfaces of the baffle member may have gas flow disrupting structures consisting of one or more protrusions and/or recesses.

We further disclose that the flow disrupter may include a gas sampling tube for sampling exhaled breath, such as a tube having an inlet opening within the baffle structure.

We further disclose that the mask may be configured whereby the gas flow disrupter and the mask body comprise mechanically interlocking structures that can be assembled without adhesives.

Directional references within the present specification and claims, such as "vertical" "horizontal" and the like are intended purely for ease of description and refer to the mask in an upright position as worn by a patient in a standing or upright sitting position.

The invention will be further explained by way of non-limiting examples and embodiments.

BRIEF DESCRIPTION OF THE DRAWINGS

FIGS. 27A-C show a table of test data for various examples according to the invention and a control.

DETAILED DESCRIPTION

Figure 1:
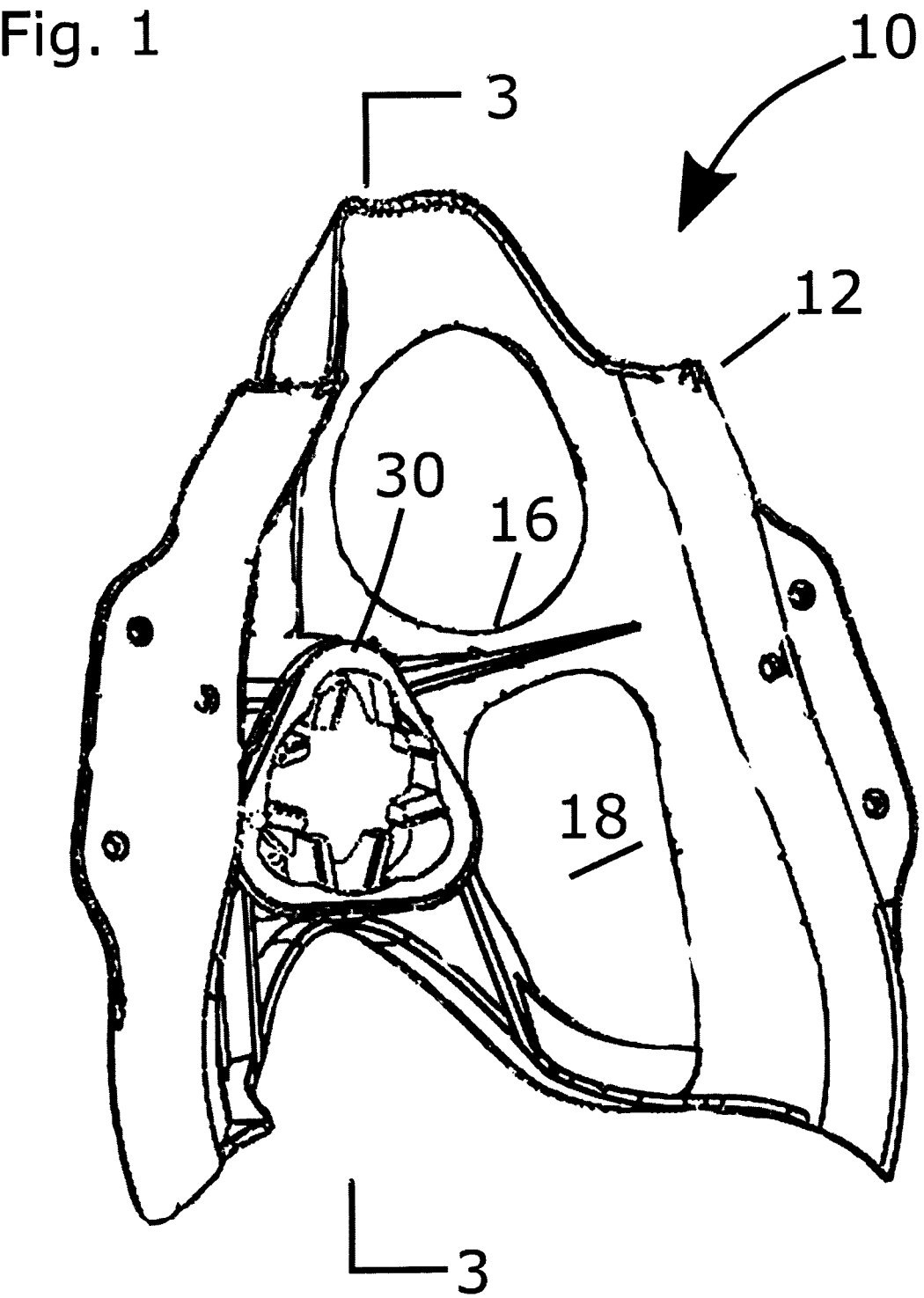
FIG. 1 is a perspective view of the interior of a mask according to one example of the present invention.
Figure 2:
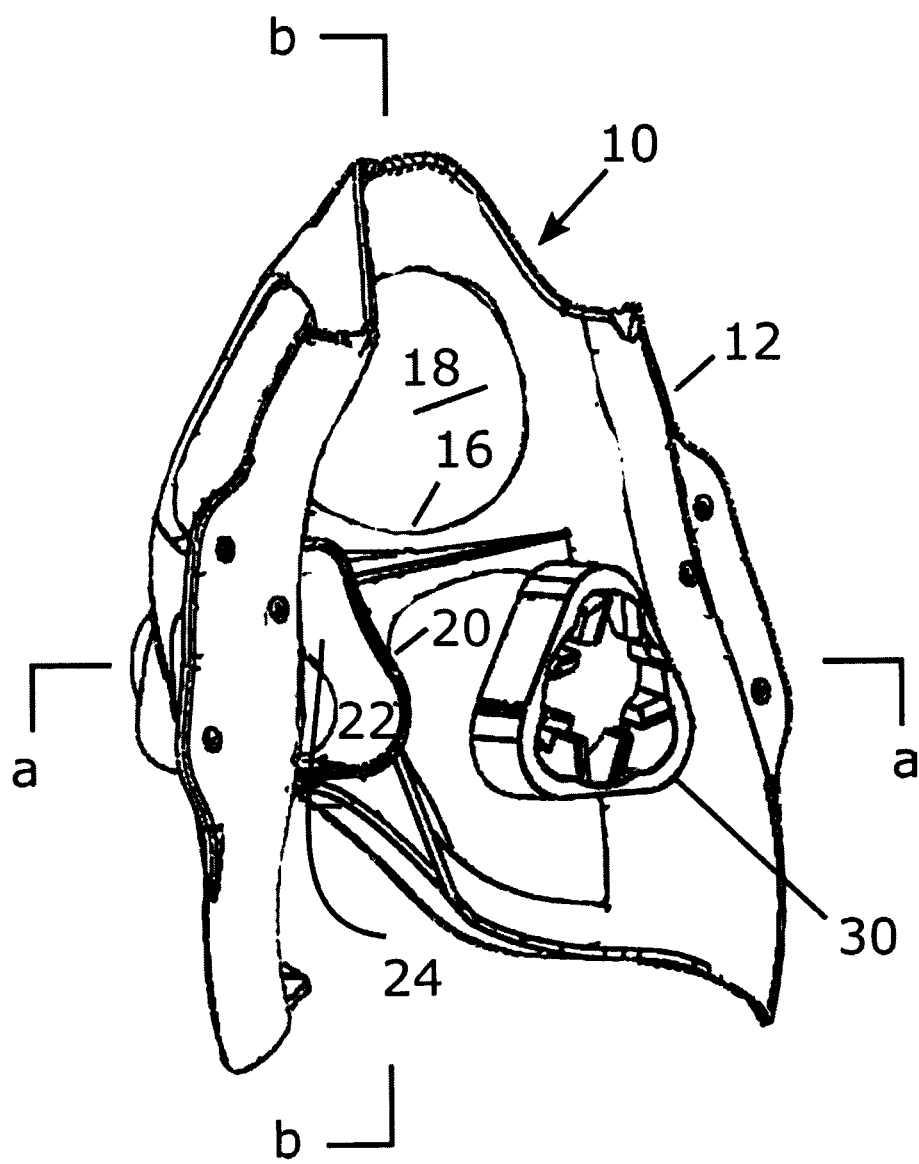
FIG. 2 is a prospective view as in FIG. 1, partially exploded to show the gas flow disruptor isolated from the mask body.
Figure 3:
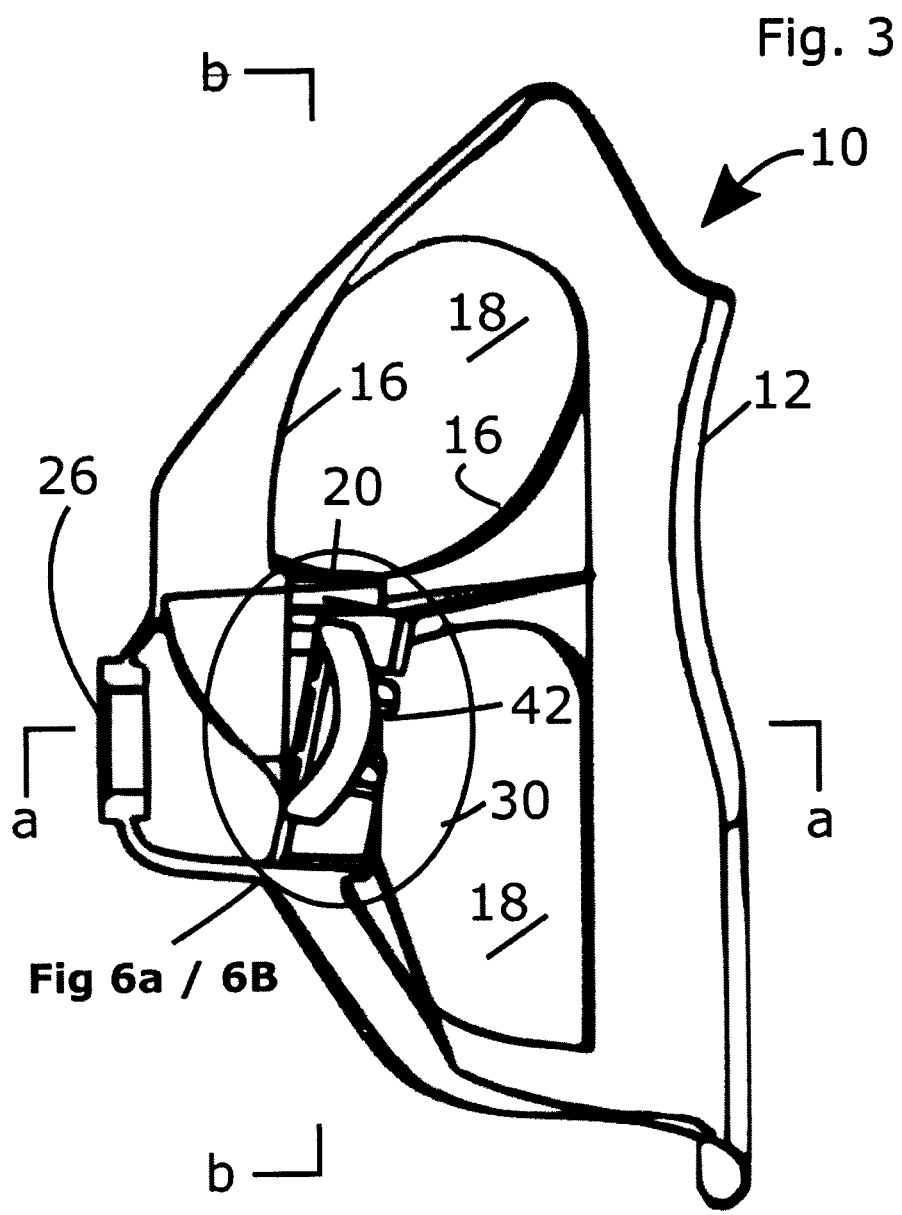
FIG. 3 is a cross sectional view along line 3-3 of FIG. 1

Referring to FIGS. 1-3, a first example according to the invention includes a mask body 10 having a substantially open configuration. The mask body 10 can be of the type described in the present inventors' U.S. Pat. No. 8,042,540. Mask body 10 includes a rim 12 for contacting the patient's face, a central forwardly-projecting nose 14, and an array of webs 16 projecting from nose 14. Webs 16 join nose 14 to rim 12, with the gaps between webs 16 defining large open spaces 18 within the mask body 10 that improve user comfort and provide other benefits for the patient and care-giver.

As shown in FIGS. 2 and 3, for purposes of describing the geometry of mask 10, a central front/rear horizontal axis a is defined by line a-a when mask 10 is oriented in an upright position and a vertical axis b is defined by line b-b in FIGS. 2 and 3, which is perpendicular to axis a.

The mask nose 14 houses a retainer structure 20 for retaining a gas flow disruptor 30, described below. The retainer structure 20 includes an inwardly projecting continuous wall 22 that surrounds and encloses an open space 24. Wall 22 is generally triangular with rounded corners, forming a substantially equilateral triangle. Other configurations of retainer structure 20 and gas flow disrupter 30 can be utilized. Space 24 opens rearwardly towards the user's face. The forward portion of continuous wall 22 merges with mask body 10 to block the forward end of open space 24. When assembled, gas flow disrupter 30 fits within space 24, leaving a gap between the front wall of nose 14 and flow disrupter 30 that effectively forms a gas manifold 23 for receiving gas flow. A central gas inlet 26 within nose 14 opens into manifold 23 upstream of flow disrupter 30. An external portion of inlet 26 is configured to connect with an external gas tube or conduit, not shown.

Gas flow from inlet 26 enters the interior of nose 14 and is discharged towards the user. Manifold 23 opens into gas flow disruptor 30. Flow disrupter 30 is configured to disrupt the gas flow from manifold 23, as described below, to generate a plume of concentrated gas towards the nose and mouth region of a user within the interior of mask body 12.

Gas flow disrupter 30 has a continuous external wall 32, having a generally triangular shape. Wall 32 is configured to fit snugly within wall 22 of retainer structure 20. As such, external wall has a generally triangular configuration with rounded corners which matches the inside surface of wall 22, whereby wall 32 has an external surface 34 for contacting the inside surface of retainer wall 22. Wall 32 has an opposing inside surface 36 that defines an inner space 37 that is open to the front and rear to permit gas to flow from manifold 23 through disrupter 30.

In some embodiments, flow disrupter 30 can be secured to retainer 20 by gluing to wall 22. In other embodiments, discussed below, a mechanical interlocking configuration is provided.

As seen in detail in FIG. 4, gas flow disruptor 30 includes a baffle assembly 40 located within its interior space 37 to partially obstruct the flow of gas and assist in generating vortices as gas is discharged towards the patient. Baffle assembly 40 includes a dome 42 and an array of fins 44 projecting radially outwardly from dome 42. Dome 42 has a concave forward face 43 that faces the front of mask 10 in the path of the gas flow, whereby gas from inlet 26 impacts on forward face 43. In some embodiments, the opposing rear face 45 of dome 42 (facing the patient's nose and mouth) is convex. Dome 42 is positioned within flow disrupter 30 to cover a substantial portion of the interior space of disrupter 30, and may be configured to block about 50% to about 90% of the area within the interior of wall 32

Dome 42 has a flat, circular rim 43 at its forward-facing, concave side. Rim 43 defines a plane that, as discussed below, can be vertical (aligned with axis b) or tilted forwardly or rearwardly relative to axis b.

As discussed below, fins 44 can be disposed within a range of angles about three axes of rotation so as to optimize gas flow within flow disrupter 30.

As seen in FIGS. 5A and 5B, inside surface of wall 32 may include inwardly scalloped recesses 36 that join with a portion of the rim of dome 42 as well as to other structures, as described below. Dome 42 is also joined to wall 32 by means of fins 44 that project radially outwardly from dome 42, to join this to the inside 20 surface of wall 32. Fins 44 comprise flat plate-like structures generally aligned with axis a in the direction of airflow. However, as discussed below, in some embodiments fins 44 can be angled relative to axis a, for generating vortices or otherwise channeling airflow through gas flow disrupter 30.

Figure 4:
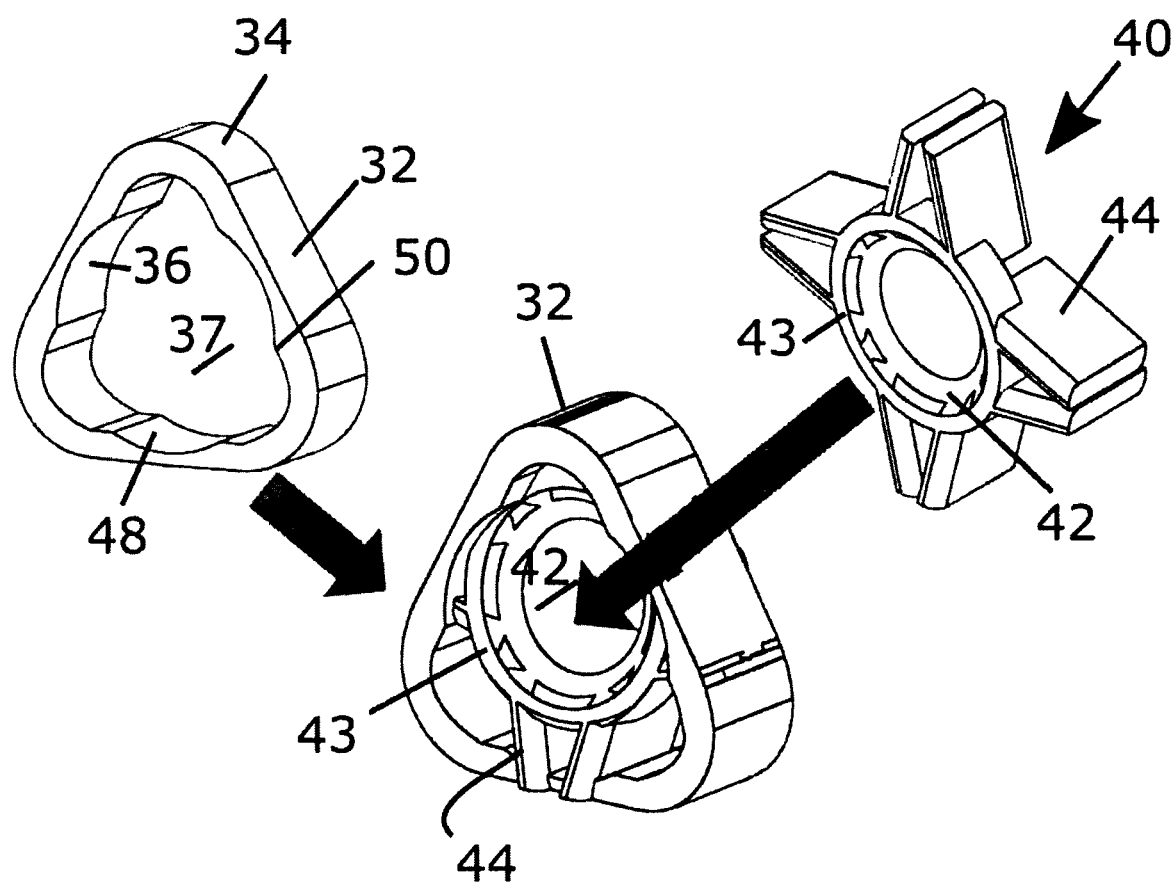
FIG. 4 is an exploded view, and perspective, of an example of the gas flow disrupter.

As seen in FIG. 4, the inside surface of wall 32 may be configured to provide additional scalloped regions 48 separated by ridges 50, which provide additional vortex generating properties, as described below.

Figure 5A:
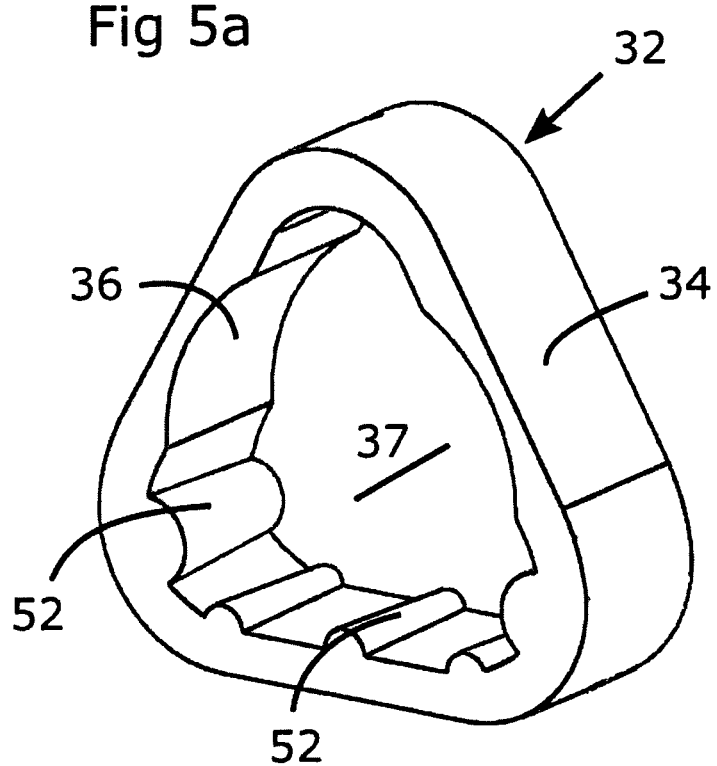
FIGS. 5A and 5B show alternative embodiments of the outer wall portion of a gas flow disrupter.
Figure 5B:
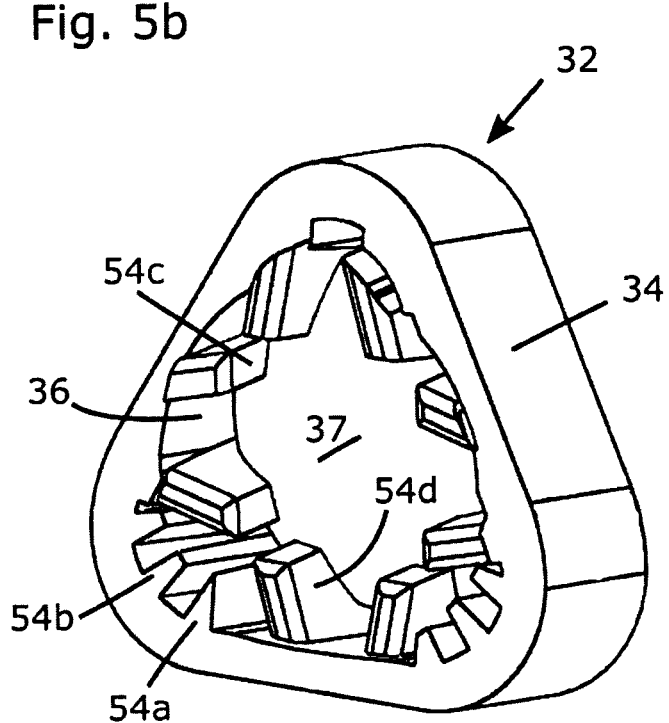

FIGS. 5A and 5B show alternative examples of structures projecting inwardly from the inside surface of retainer wall 22. In FIG. 5A, the inward projections consist of rounded ribs 52. In FIG. 5B, the projections consist of ribs having triangular, rectangular and/or trapezoid cross sections 54a-c, and/or tooth-like trapezoidal projections 54d. The orientation of these projections may be aligned with axis a, so as to be aligned with the general direction of airflow flowing through disrupter 30, or angled.

Figure 6A:
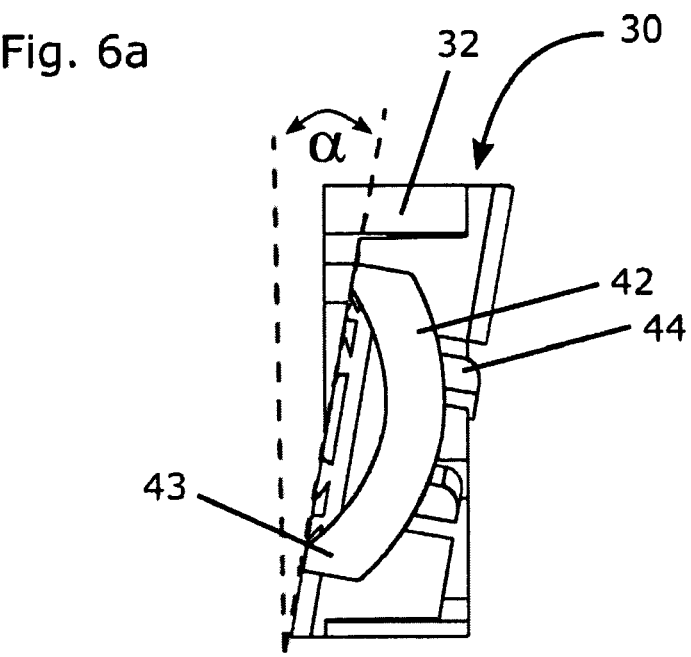
FIGS. 6A and 6B show enlarged cross sectional views of the circled region of FIG. 3, showing alternative embodiments of a gas flow disrupter.
Figure 6B:
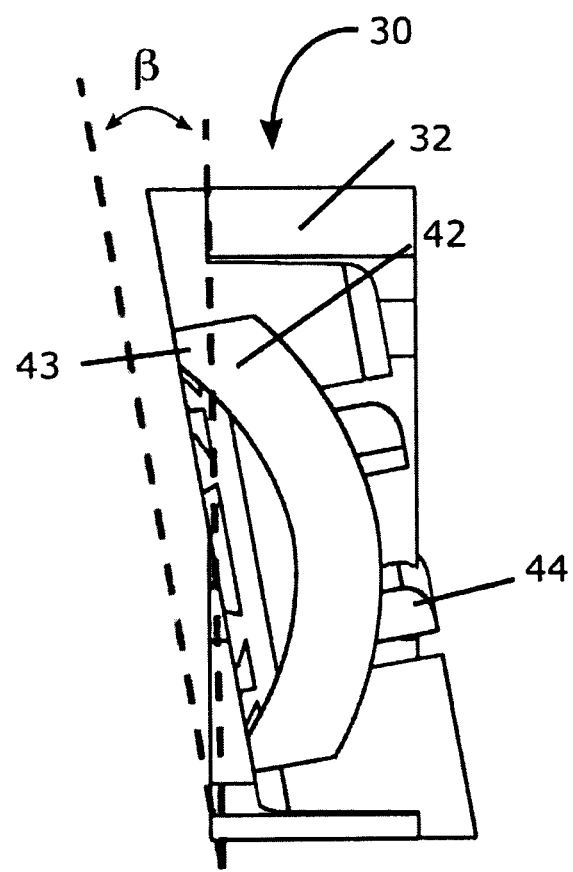
Figure 7A:
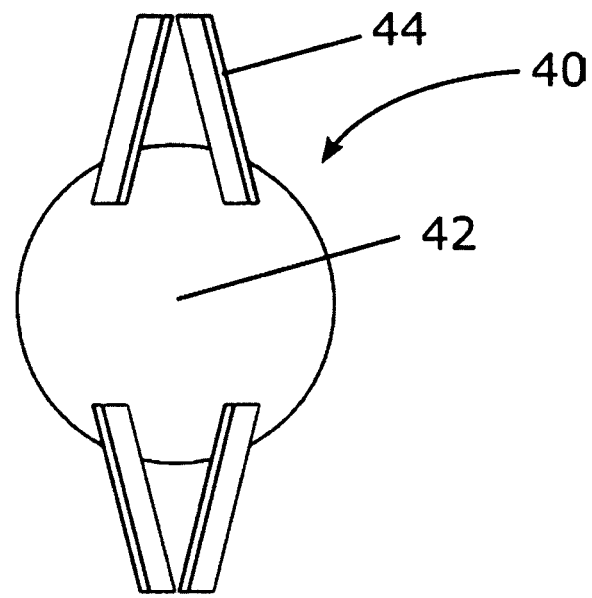
FIGS. 7A-F show alternative embodiments, in plan view, of the vortex generator portion of the gas flow disrupter.
Figure 7B:
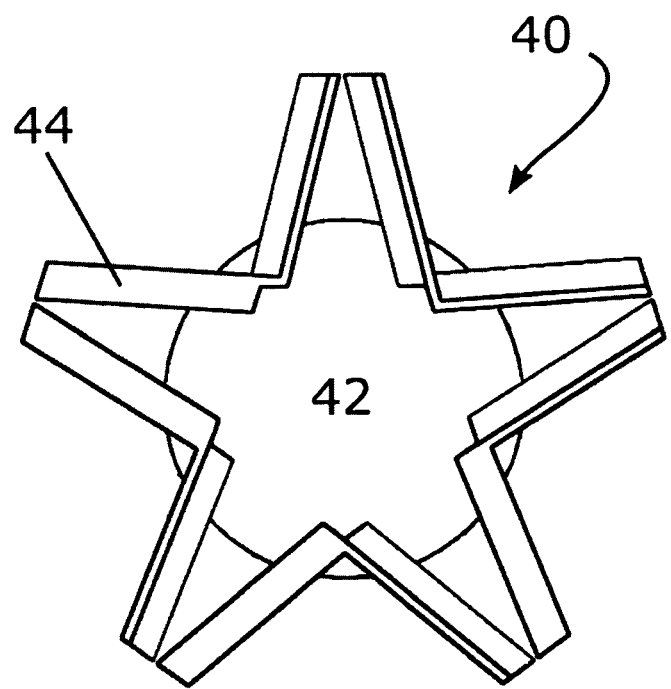
Figure 7C:
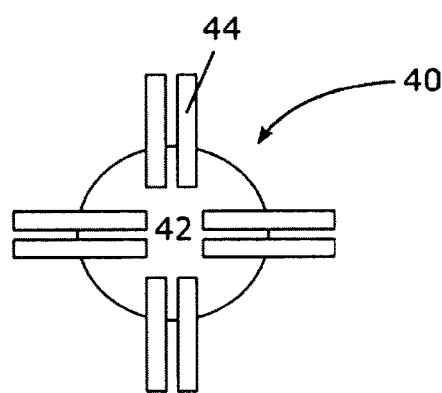
Figure 7D:
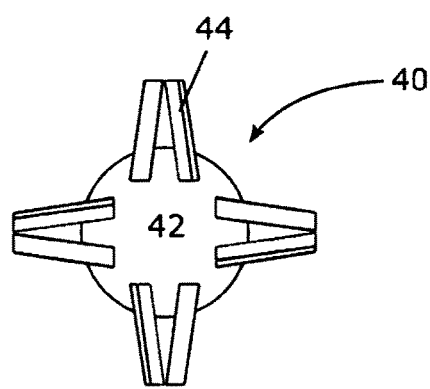
Figure 7E:
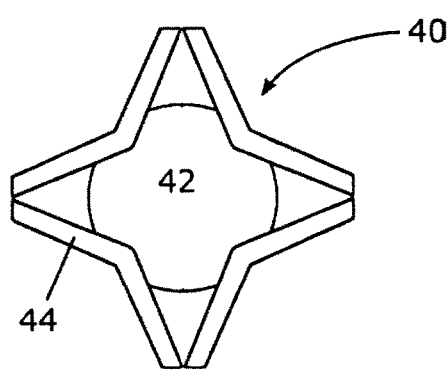
Figure 7F:
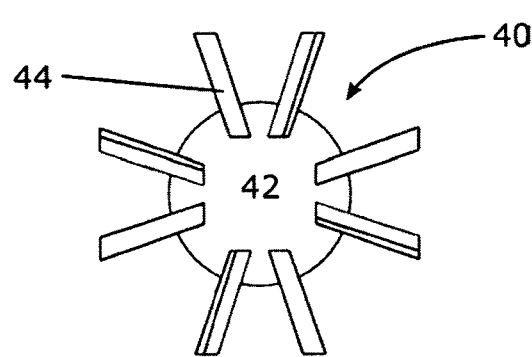

Turning to FIGS. 6A and 6B, dome 42 can be oriented in a forwardly-tilting configuration as seen in FIG. 6A, in which dome 42 angles rearwardly by an angle α. Alternatively, dome 42 may have a rearwardly tilting configuration of FIG. 6B in which dome 42 is angled at angle β. In various embodiments, angles α and β are up to about 20° from vertical axis b, or up to about 40° from vertical axis b, for example about 5°, about 10°, about 20° or between 20° and 40°. Alternatively, dome 42 is in an intermediate position in which dome 42 is generally upright in relation to axis b. The different degrees of tilt of dome 42 have the effect of directing airflow either towards the nose or mouth of a user or equally balanced between these two when dome 42 is essentially vertical.

FIGS. 7A through 7F show various embodiments of baffle assembly 40, which can achieve different gas flow properties. As seen in these figures, fins 44 can be arranged in V-shaped or parallel pairs or non-paired configurations. The baffle assembly 40 may be provided with four such fins 44, arranged in two opposing structures, as in FIG. 7A, or alternatively three, four, five or more such paired fins 44. The paired fins 44 in V-shaped configurations may have a narrow spread, for example as in FIG. 7D, thereby leaving gaps between the fin pairs, or alternatively the spread may be wide so as to form an essentially continuous structure composed of fins 44 radially surrounding dome 42. Fins 44 may be angled at a tangent relative to dome 42 within a range of angles of between up to 45° away from a radius of dome 42. In one example, fins 44 are angled relative to a radius of dome 42 (i.e. at a tangent to dome 42) at about 14°. In that example, the pairs of fins 44 are thus disposed in a V-shaped configuration at angle of about 28° from each other. Alternatively, fins 44 may project radially outwardly from dome 42, either in a paired parallel arrangement as in FIG. 7c or a non-paired array as in FIG. 7 F.

Figure 8A:
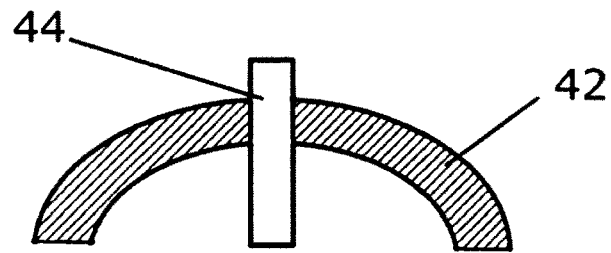
FIGS. 8A-8D show cross sectional views of alternative embodiments of the vortex generator.
Figure 8B:
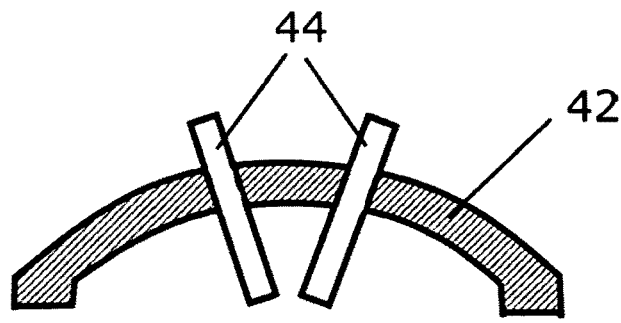
Figure 8C:
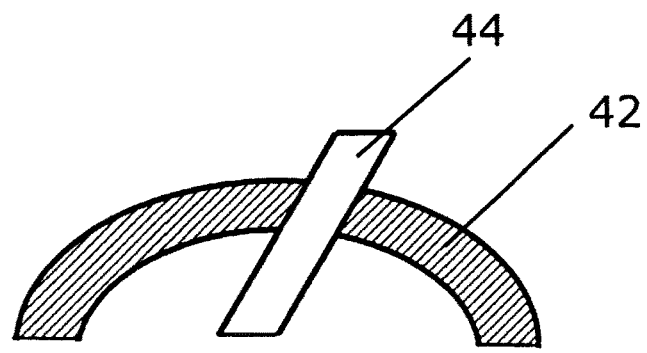
Figure 8D:
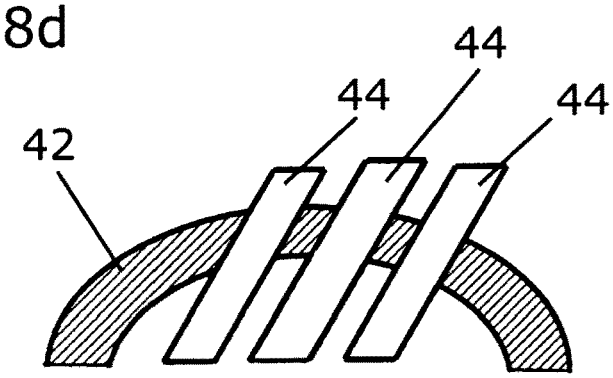

Fins 44 can be configured to be aligned with axis a, or alternatively angled relative to axis a, as seen in FIGS. 8B-8D. In some embodiments, fins 44 can be angled within a range up to 45° or in a range of 6°-35°, relative to horizontal axis a. In some examples, fins 44 are perpendicular to a plane defined by the rim 43 of dome 42. For example, if dome 42 is vertical, with no tilt, fins 44 are likewise aligned with a vertical plane; whereas if dome 42 is tilted relative to a vertical plane, fins 42 are likewise tilted by the same degree to the vertical plane. As discussed above, this tilt can be forwardly or rearwardly, and up to about 40° from a vertical plane.

In one example, dome 42 and fins 44 are tilted downwardly or upwardly from the vertical by about 10°.

Figure 9A:
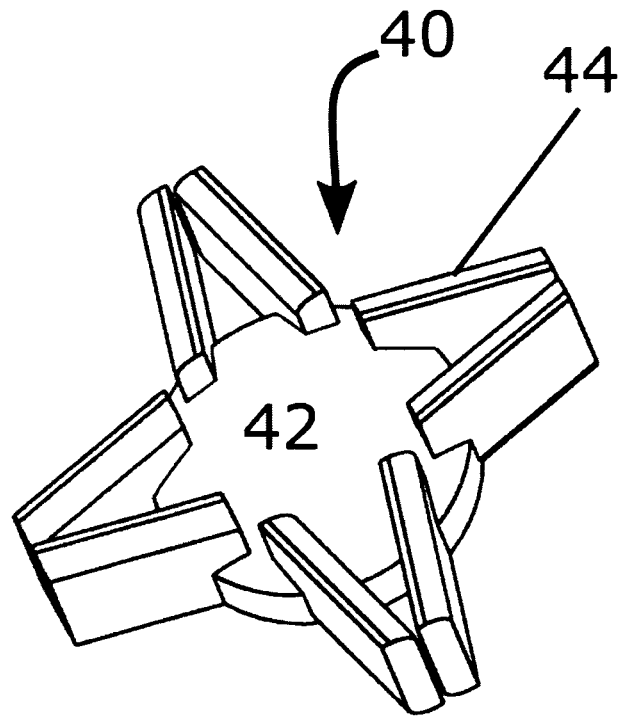
FIGS. 9A and 9B show further alternative embodiments of the vortex generator.
Figure 9B:
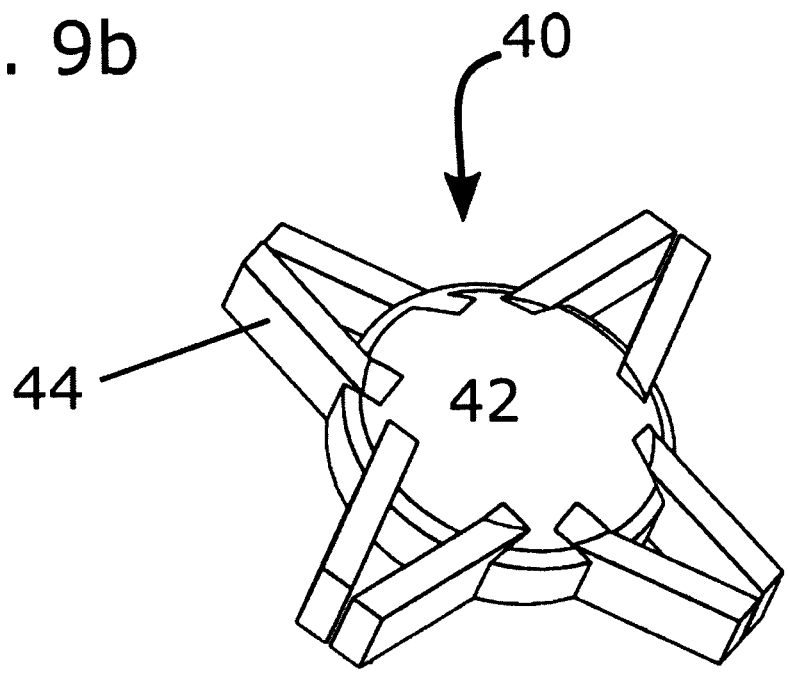

Fins 44 have a depth, as measured along axis "a" from the front to the rear of gas flow disrupter 30, which can vary in different embodiments to vary the gas flow properties. As seen in FIG. 9A, fins 44 have a relatively large depth which permits them to project rearwardly and/or forwardly from dome 42. FIG. 9B shows an example in which the fins have a smaller depth and do not project forwardly from dome 42.

Figure 10A:
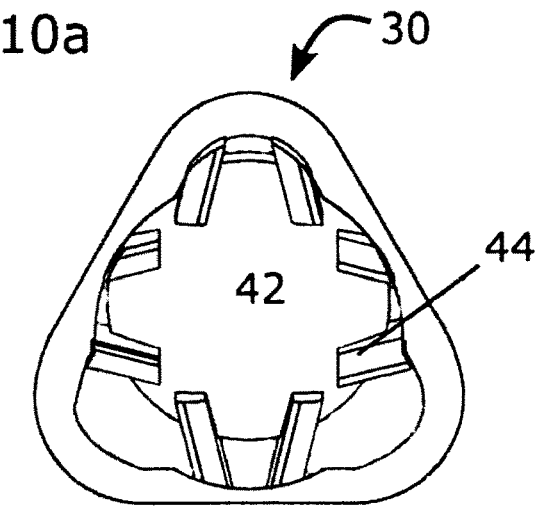
FIGS. 10A-10C show alternative embodiments of the gas flow disruptor, in plan view, showing in particular different relative sizes of the central dome-shaped baffle.
Figure 10B:
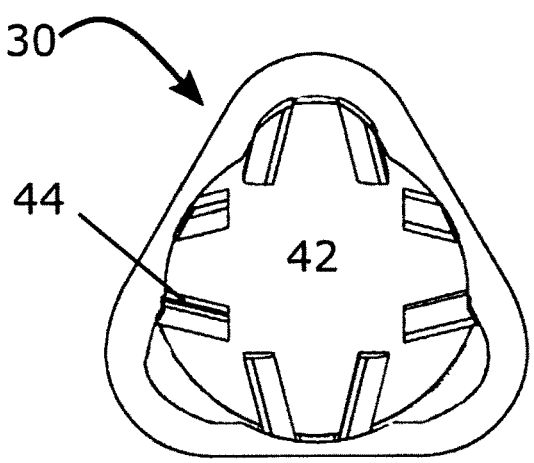
Figure 10C:
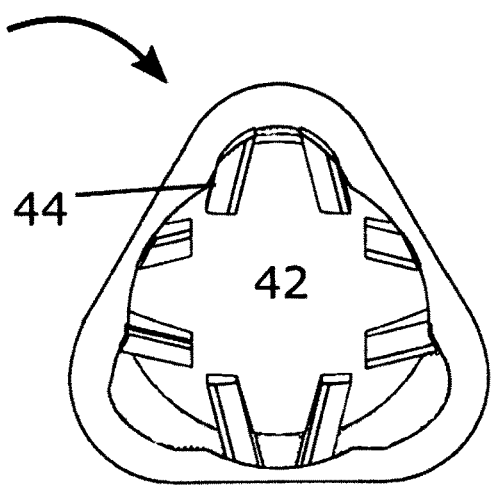

FIGS. 10a to 10c show examples in which dome 42 has different surface areas, so as to block different proportions gas flow within of flow disrupter 30. FIG. 10A shows a dome 42 having a relatively small surface area, which blocks approximately 50% of the inside space of disrupter 30. FIG. 10B shows a larger dome 42, which blocks approximately 90%. FIG. 10C shows an intermediate-size baffle 42 which blocks an intermediate percentage. The size of baffle 42 may be selected based on expected gas flow rates for the mask design, to provide a mask that minimizes the loss of air escaping from mask 10 when gas is delivered within the target flow rates.

Figure 11A:
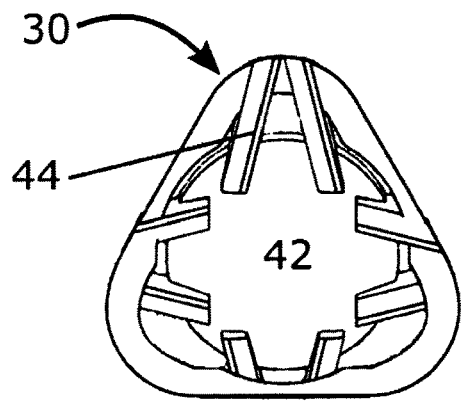
FIGS. 11A-11C show alternative embodiments in plan view of the gas flow disruptor, showing in particular different relative locations within the disrupter of the central dome-shaped baffle.
Figure 11B:
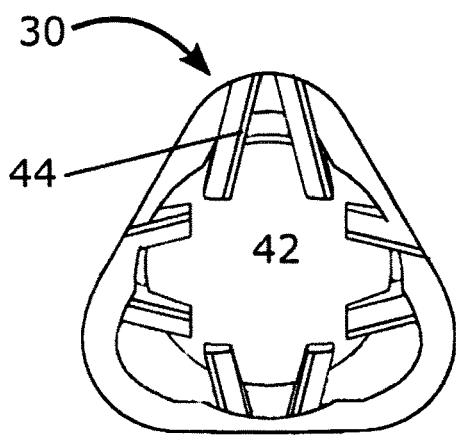
Figure 11C:
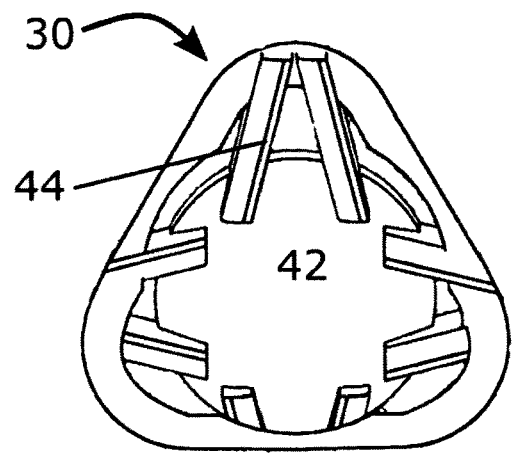

FIGS. 11A-11C show examples in which dome 42 is positioned in different relative locations within the flow disruptor 30. In FIG. 11 A, dome 42 substantially centrally located within flow disrupter 30. In FIG. 11B, dome 42 is located more upwardly and closer to the top of disrupter 30, and in FIG. 11 C, dome 42 is located more downwardly within disrupter 30. The position of dome 42 within gas flow disrupter 30 can channel more airflow downwardly towards the user's mouth, when dome 42 is positioned in a relatively high position within flow disrupter 30. Dome 42 can instead direct airflow upwardly towards the user's nostrils when dome 42 is positioned in a lower position which leaves more open space in the upper portion of the flow disruptor for gas flow. Alternatively, the gas flow can be evenly balanced between the nose and mouth when the dome 42 is centrally located within flow disrupter 30.

Figure 12B:
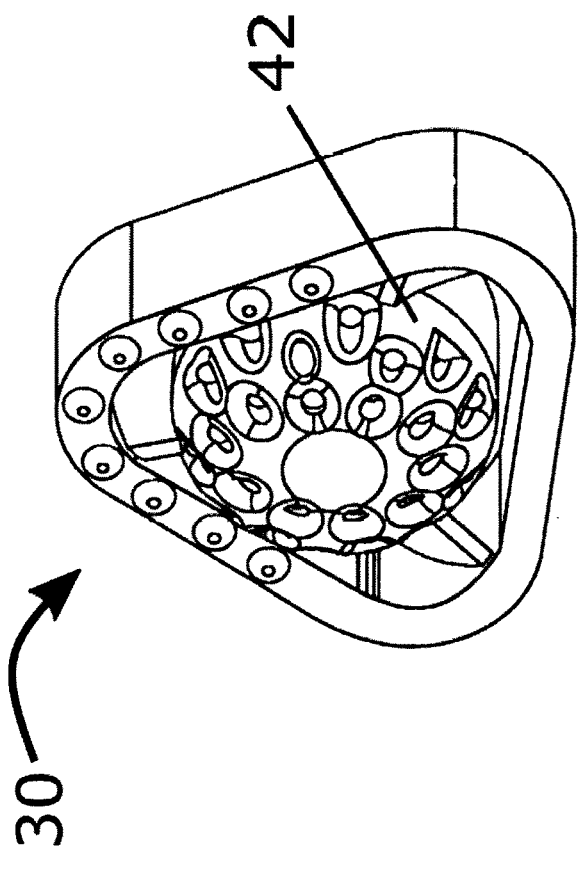
FIGS. 12A-12D are perspective views of alternative embodiments of the gas flow disrupter, showing optional structural elements on the surface of the central baffle.
Figure 12A:
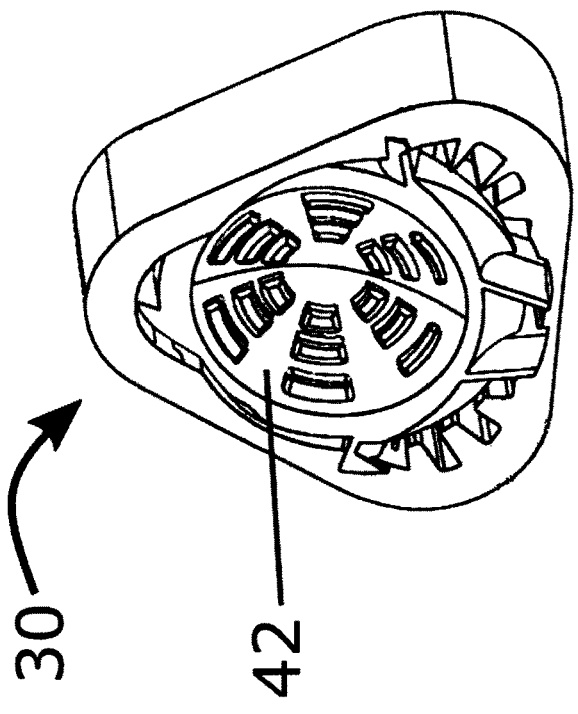
Figure 12C:
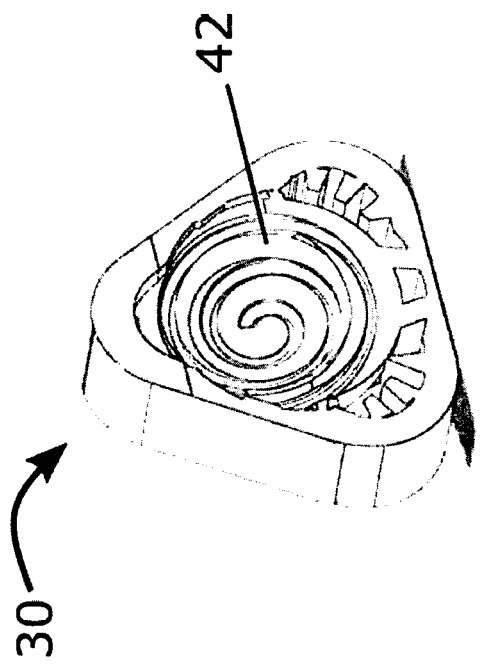
Figure 12D:
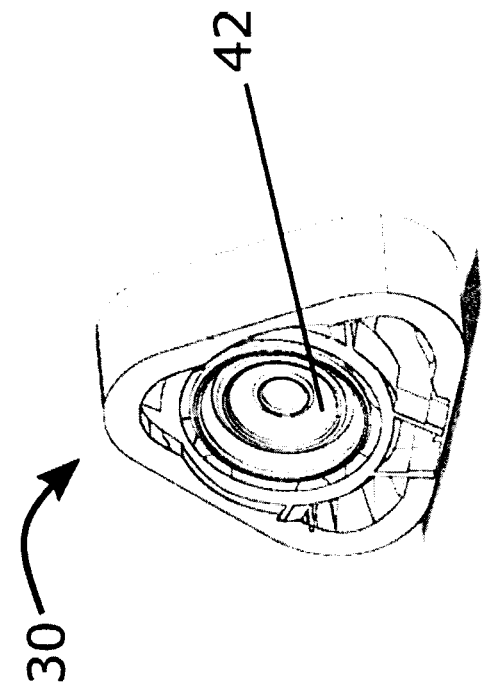

As seen in FIGS. 12a-12 D, in some embodiments the convex and/or concave surfaces 43/45 of dome 42 may be provided with a texture and/or projecting or recessed structures or the like, to control air flow patterns and gas turbulence generation. Such structures can consist of ribs, grooves, swirls, domes, or other members of a wide range of configurations. Furthermore, structural members of a similar configuration may instead or in addition be provided on flow disrupter wall 32.

Figure 13:
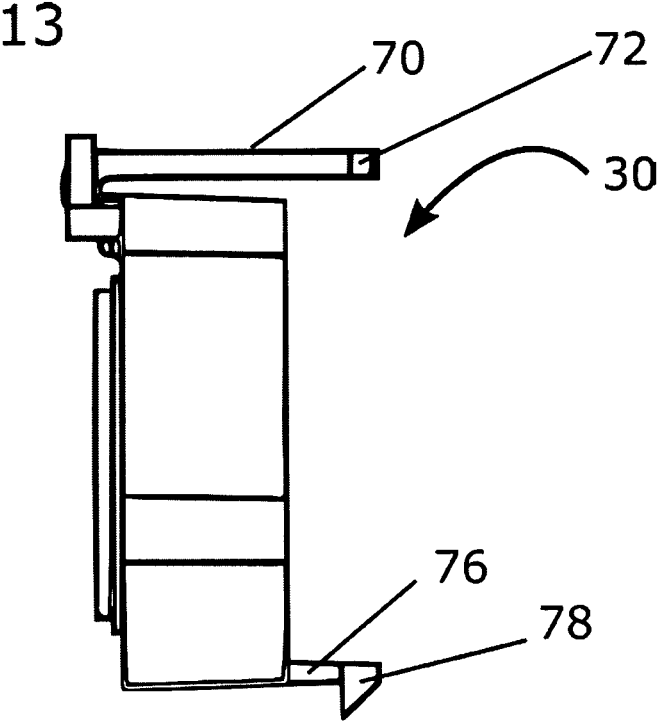
FIG. 13 is a side elevation view of a further example of the gas flow disruptor.
Figure 14:
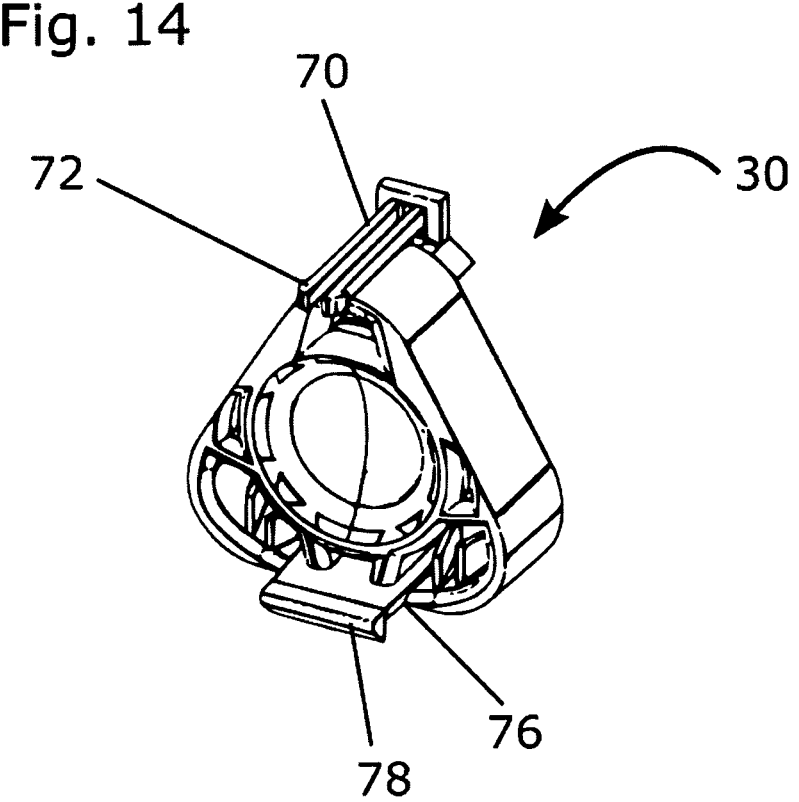
FIG. 14 as a perspective view of the example shown in FIG. 13.
Figure 15A:
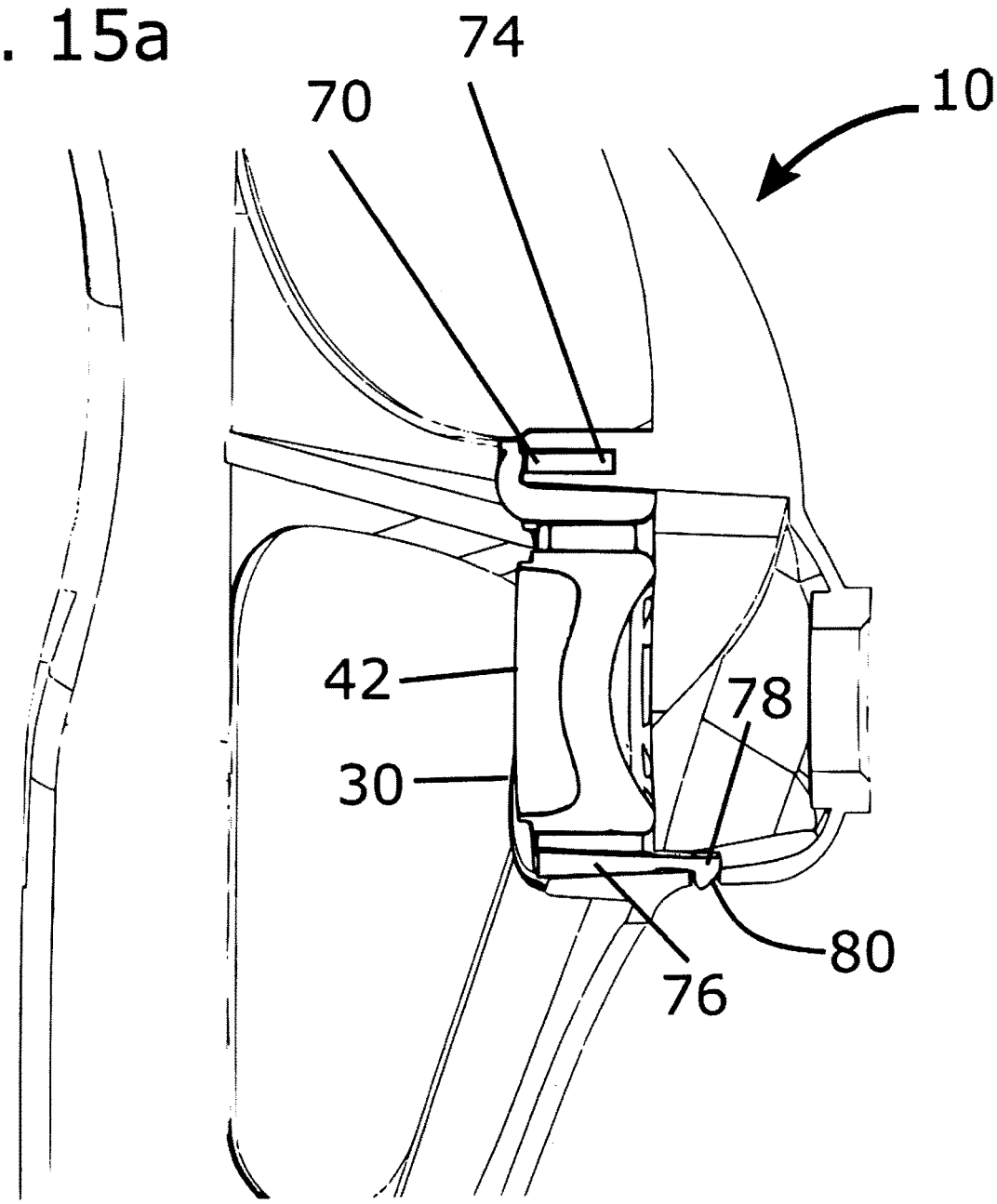
FIGS. 15A and 15B show cross-sectional and exploded perspective views, respectively, of a portion of a mask according to the embodiment of FIG. 13.
Figure 15B:
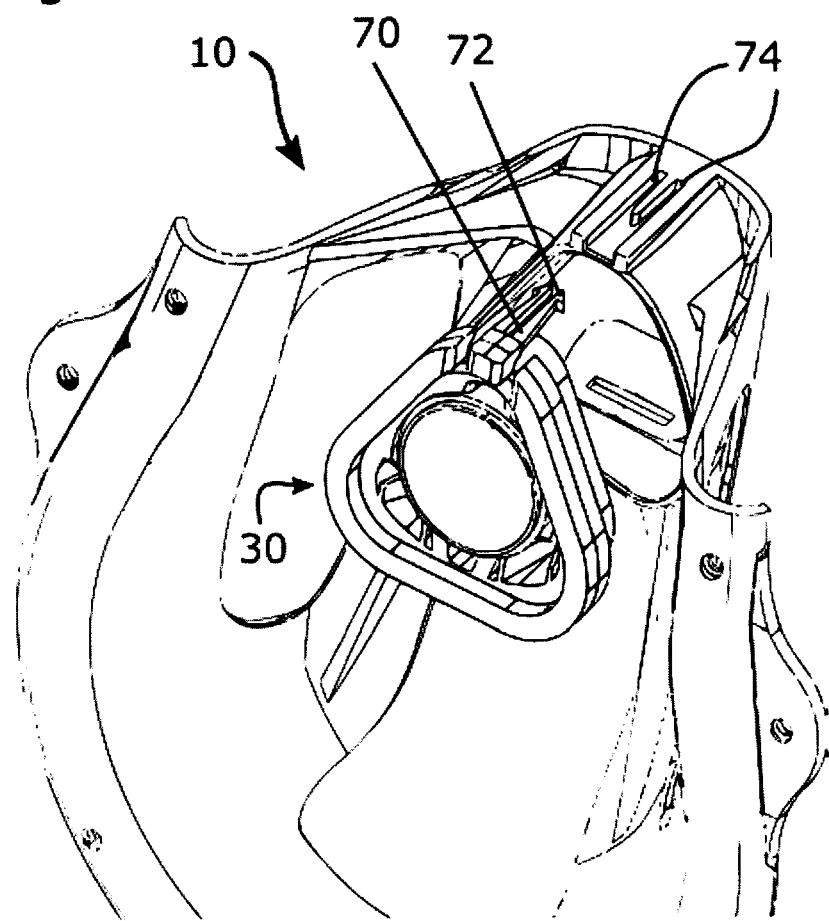

Referring to FIGS. 13 through 15, alternative examples are shown in which flow disrupter 30 is connected to mask body 10 with mechanical interlock components. This permits flow disrupter 30 to be attached to mask body 10 without the need for gluing. According to this example, flow disrupter 30 includes a pair of forwardly projecting prongs 70 projecting from an upper portion of flow disrupter wall 32. Prongs 70 are configured to flex in a horizontal direction for squeezing together. Prongs 70 each terminate at their free ends in an enlarged arrowhead-shaped head 72 configured to engage a corresponding opening 74 in the flow disruptor retainer for a snap lock engagement to attach flow disrupter 30 to mask body 10. Heads 72 project laterally outwardly to engage horizontal openings 74 within nose 14 of mask body 10. Flow disrupter 30 further comprises a single lower prong 76 that projects forwardly from wall 32 and terminates at its forward end in a similar arrowhead-shaped prong head 78, configured to engage a corresponding opening 80 in the flow disruptor retainer 20 for a snap lock engagement. Lower prong 76 is configured to flex vertically to engage vertically-aligned opening 80. The flexibility of the respective prongs 70 and 76 permits these to be snapped locked into receptacles 74 and 80 within the retainer 20, which occurs by pushing the gas flow disruptor 30 forwardly into the interior space of the retainer wall 22 until the flow disruptor 30 snap locks into position. The arrowhead-shaped prong heads 72 and 78 lock the flow disrupter 30 in a non-releasable fashion. Retainer structure 20 within the mask body 10 contains channels and receptacles that are configured to receive the corresponding prong components of the flow disrupter 30.

Figure 16:
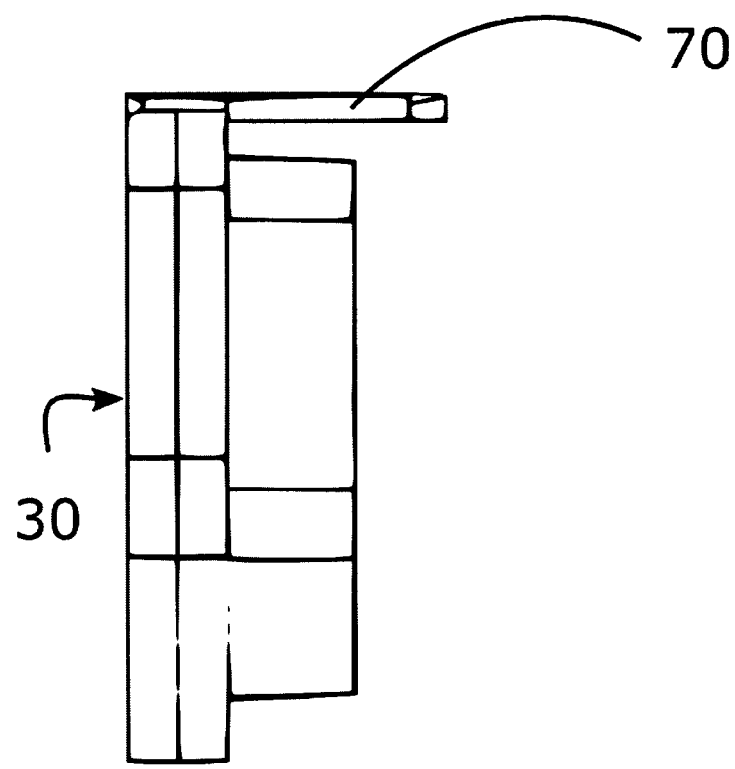
FIG. 16 is a side elevational view of a further example of the gas flow disruptor.
Figure 17:
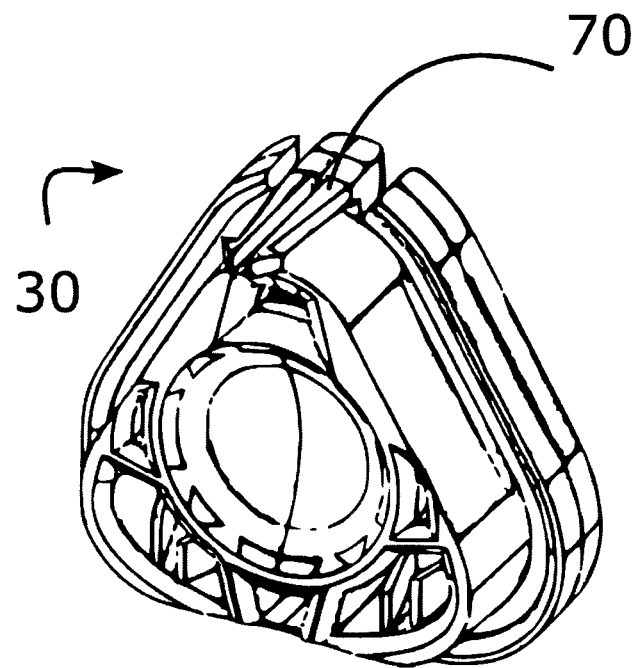
FIG. 17 is a perspective view of the example shown in FIG. 16.
Figure 18:
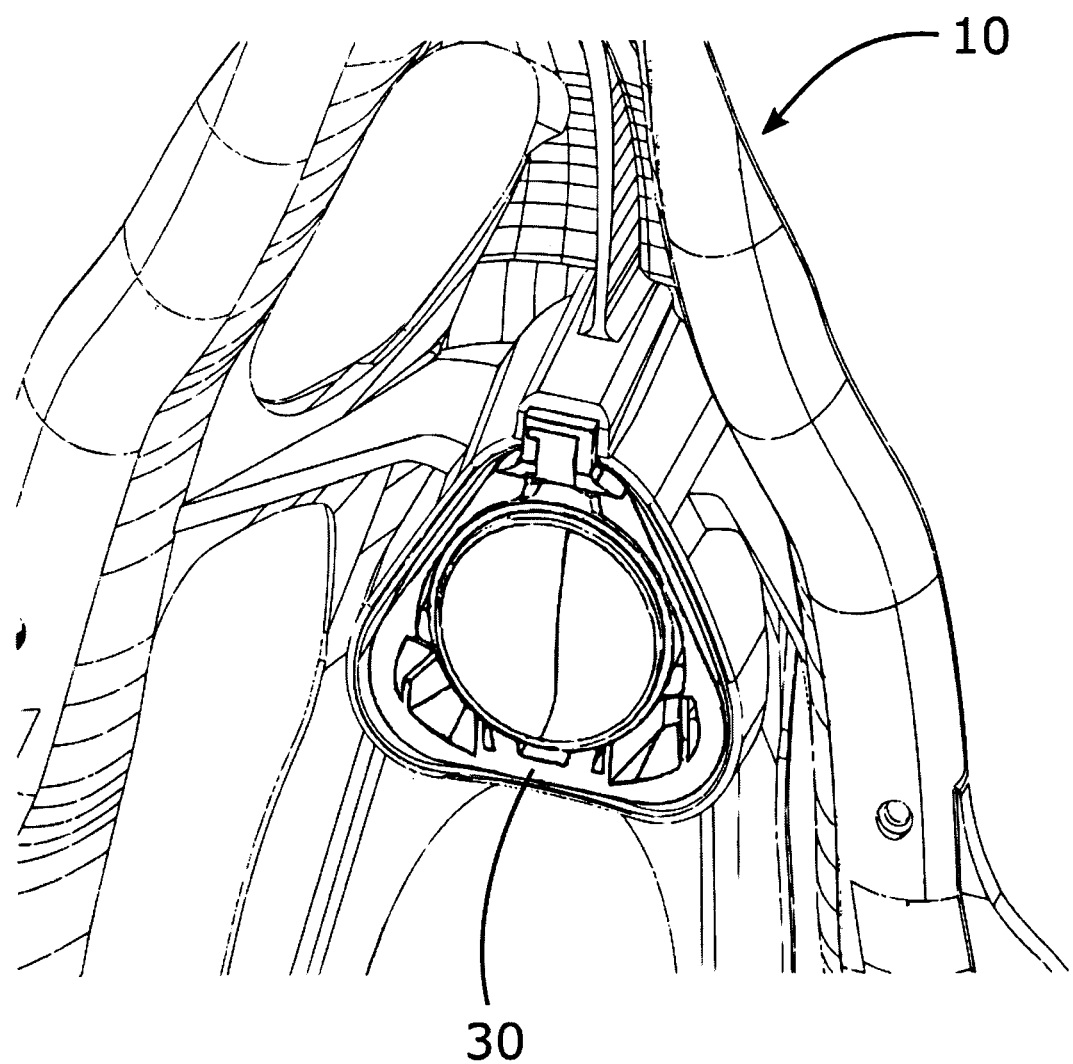
FIG. 18 is a perspective view have a mask, from the interior of the mask body, showing the gas flow disrupter of FIG. 16 mounted within the mask body.
Figure 19:
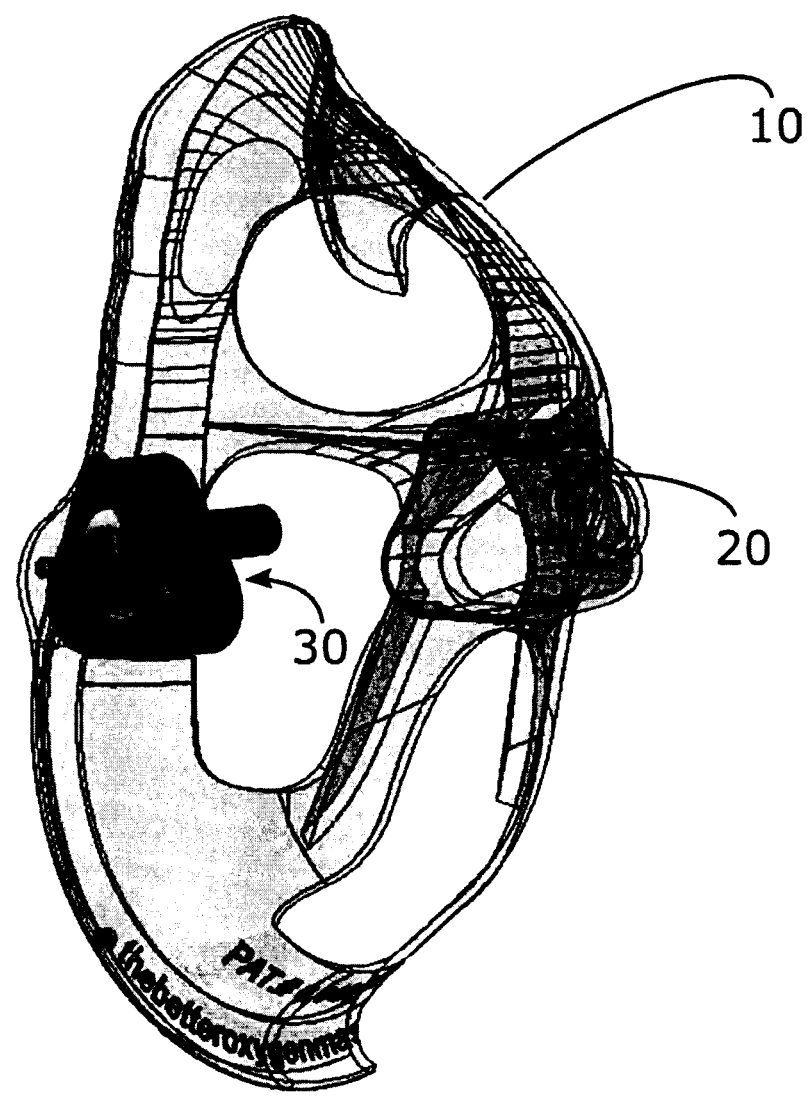
FIG. 19 is a perspective view, partially in section and partially exploded, showing a further embodiment in which the gas flow disrupter includes a $CO_2$ capture inlet.
Figure 20:
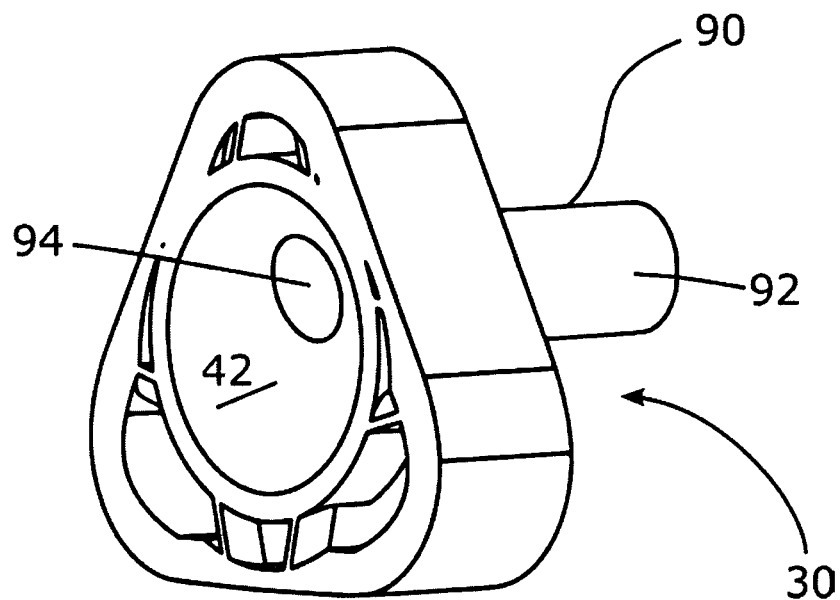
FIG. 20 is a perspective view of the gas flow disrupter according to FIG. 19.
Figure 21:
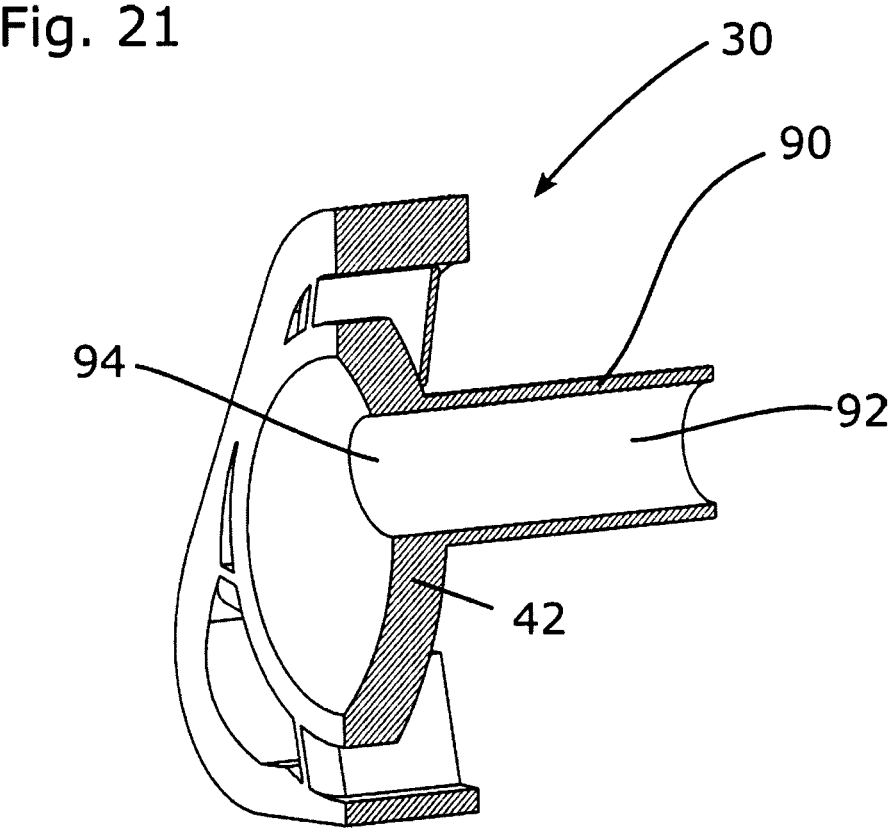
FIG. 21 is a partial sectional view of the gas flow disrupter of FIG. 20.

FIGS. 16-18 show is similar embodiment of the above, with the retainer 30 having only paired upper prongs 70. This configuration provides a somewhat less complex manufacturing process and with sufficient tolerances is sufficient to retain the flow disrupter in position, depending on the ultimate use of the mask.

Figure 22:
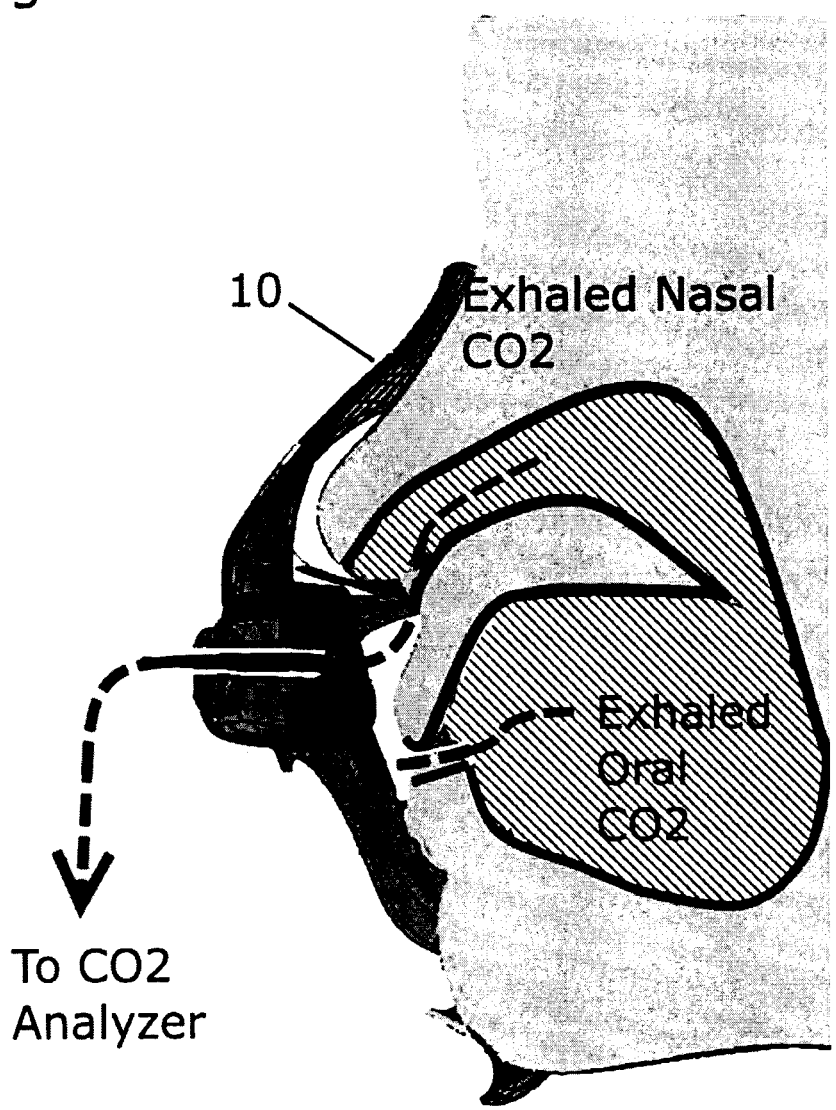
FIG. 22 is a cross-sectional view of the mask of FIG. 19, in use with a patient.

FIGS. 19 to 22 to show a further embodiment in which flow disruptor 30 incorporates a $CO_2$ collector 90, which is configured to receive a portion of the $CO_2$ exhaled by a patient for sampling purposes. $CO_2$ collector 90 comprises a tube 92, which has an inlet 94 at its rearward end. Inlet 94 opens within dome 42. In one embodiment, inlet 94 is in a generally central location within dome 42, which is a position of relatively low gas pressure within mask 10. Tube 92 projects forwardly through the front of nose 14 for connection to a $CO_2$ outlet tube, not shown. The $CO_2$ outlet tube may in turn connect to a $CO_2$ analyzer, not shown. As seen in FIG. 22, $CO_2$ collector 90 receives and collects the sample of $CO_2$ exhaled from the patient's nose and mouth. In this embodiment, the concave surface of dome 42 faces the patient, thereby reversing the orientation of dome 42 over the previous examples that do not include the $CO_2$ collector.

Figure 23A:
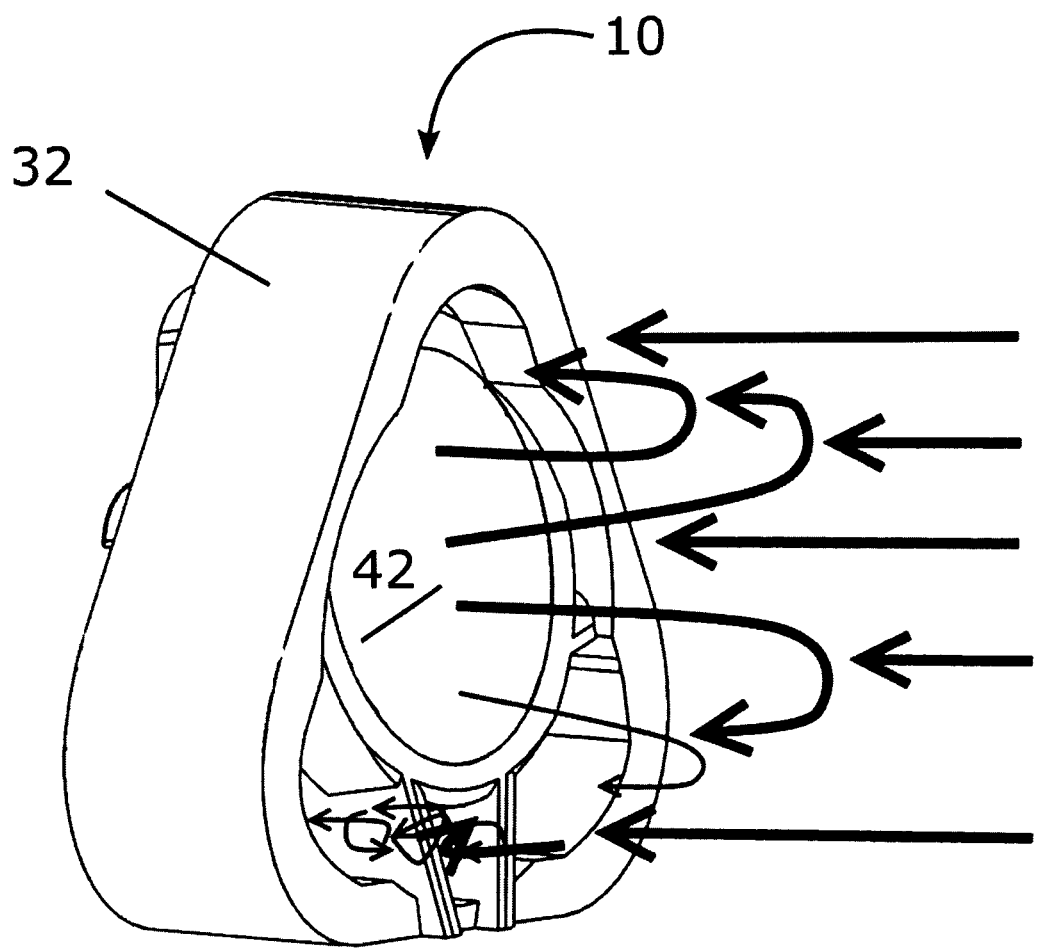
FIGS. 23A and B are perspective views, partially in sectional view in FIG. 23B, showing a gas flow pattern generated by a gas flow disrupter.

FIGS. 23A and B schematically illustrate gas flow patterns generated by flow disruptor 30. FIG. 23A shows a typical gas flow upstream of flow disrupter 30, in which a portion of the gas flow from the gas inlet impacts on the upstream surface of dome 42 and rebounds into the open manifold portion of nose 14. This has the effect of increasing gas pressure within the manifold region 23 within nose 14. The trapped gas in turn escapes through flow disrupter 30 around the perimeter of dome 42, through gaps between dome 42 and the inside surface of flow disrupter wall 32. The increased gas pressure arising from the rebound effect of dome 42, effectively increases the flow rate through flow disrupter 30.

Figure 23B:
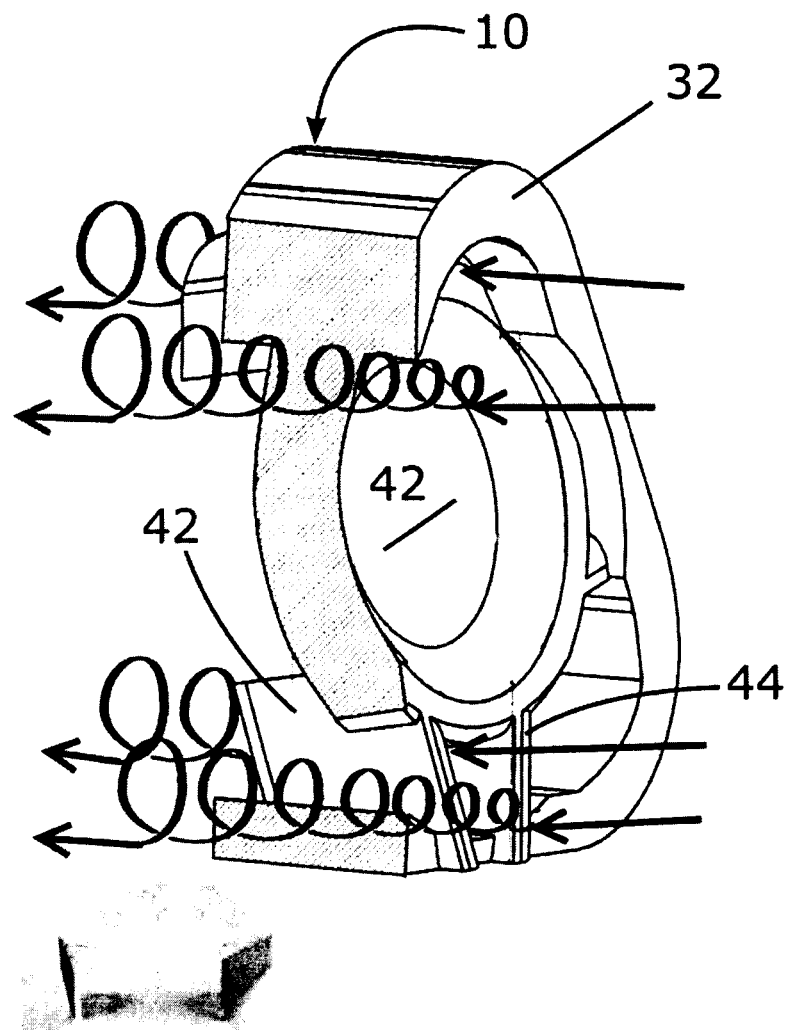

FIG. 23B shows a gas flow vortex pattern generated by fins 44 and other structures incorporated into flow disrupter 30 that are located in the path of gas flow around the perimeter of dome 42. As seen from FIG. 23, fins 44 and other structures of flow disrupter 30 tend to generate vortices as the gas flows through flow disrupter 30 towards the patient.

Figure 24A:
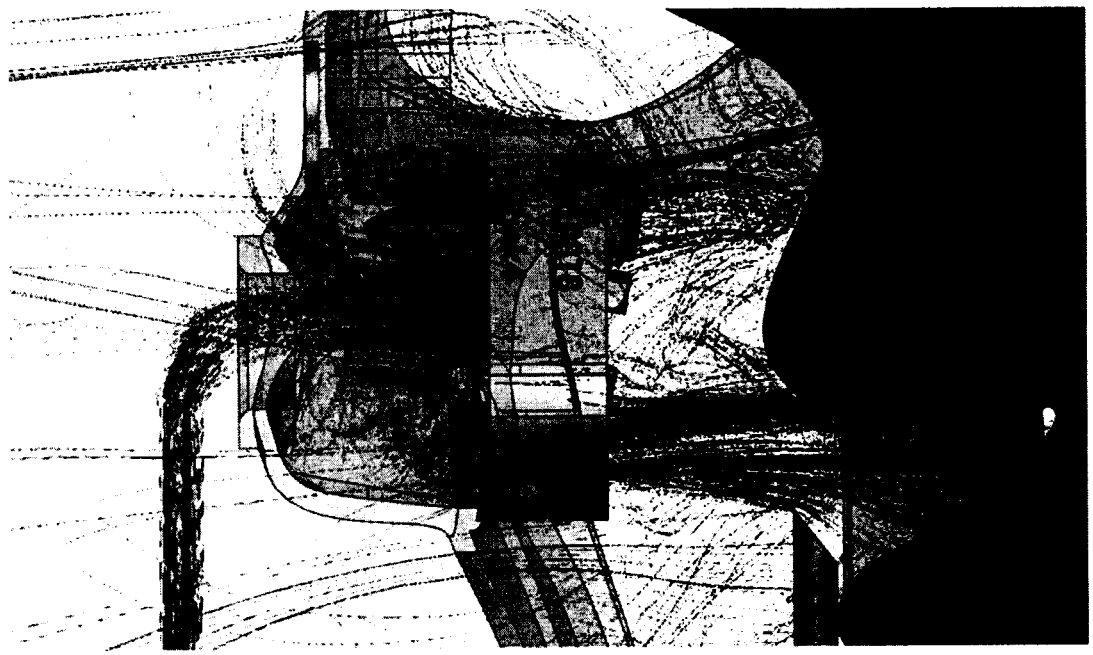
FIGS. 24A and B are further views showing simulated gas flow within a mask.

FIGS. 24A and B show simulations of gas flow through mask 10. In FIG. 24A, gas flow is shown in an embodiment in which dome 42 is configured and positioned to provide increased gas flow towards the user's mouth. In this embodiment, a majority of the gas flow is channeled through flow disrupter 30 in a generally downward direction towards the user's mouth.

Figure 24B:
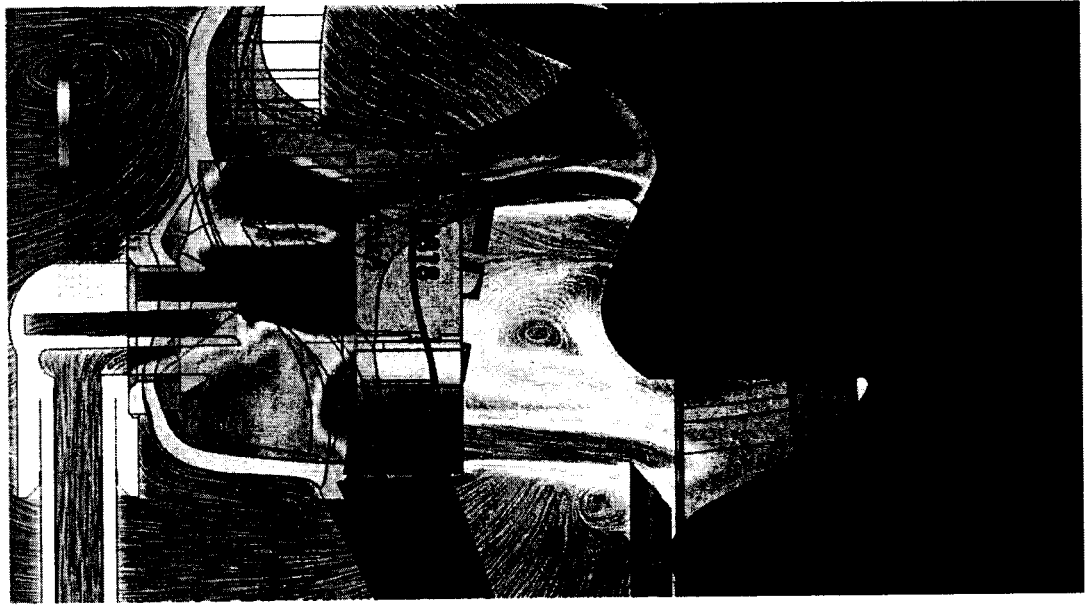

FIG. 24B shows an embodiment in which dome 42 is configured to direct the gas flow in a balanced fashion such that similar gas flow rates are directed upwardly towards the user's nose and downwards towards the user's mouth. As seen in FIG. 24B, gas flow is directed into discreet upper and lower streams with an area of relatively low pressure between these.

Figure 25:
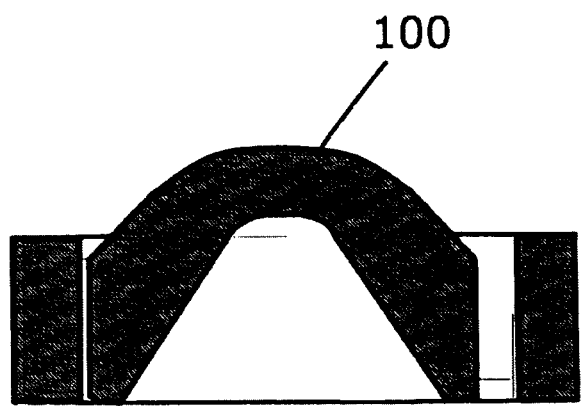
FIG. 25 is a cross sectional view of a further embodiment of the gas flow disrupter, showing an alternative configuration of the central baffle.
Figure 26:
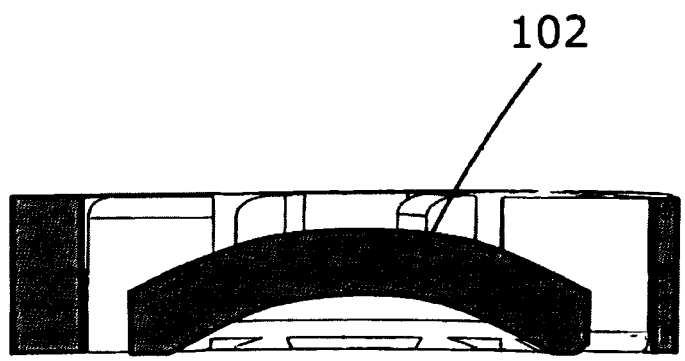
FIG. 26 is a further cross-sectional view of the flow disrupter, showing a still further configuration of the baffle assembly of the flow disrupter.

FIGS. 25 and 26 show alternative embodiments of the dome within gas flow disruptor 30. In FIG. 25, dome 100 is configured as a relatively deep dish, with a front to rear depth which is approximately 50% of the diameter of dome 100. FIG. 26 shows a shallower dome 102, in which the front to rear depth is approximately 17% of the diameter of dome 102. In other embodiments, the dome may comprise an intermediate depth between these two.

Example 1

Tests were performed on different mask configurations according to examples of the invention, and a control. The tests showed gas concentrations at a patient's nose and mouth for the tested masks.

Figures 27A, 27B:
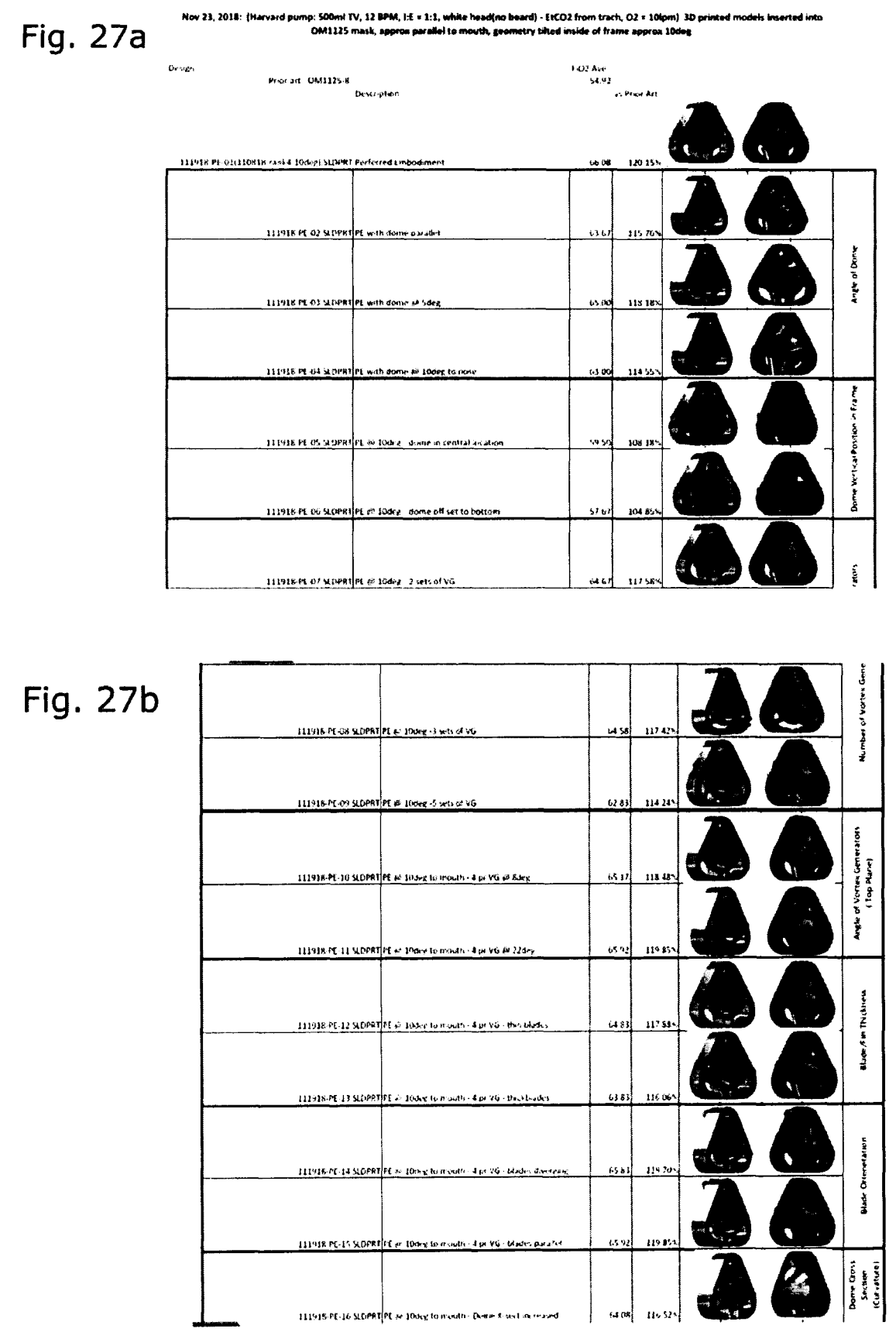
Figure 27C:
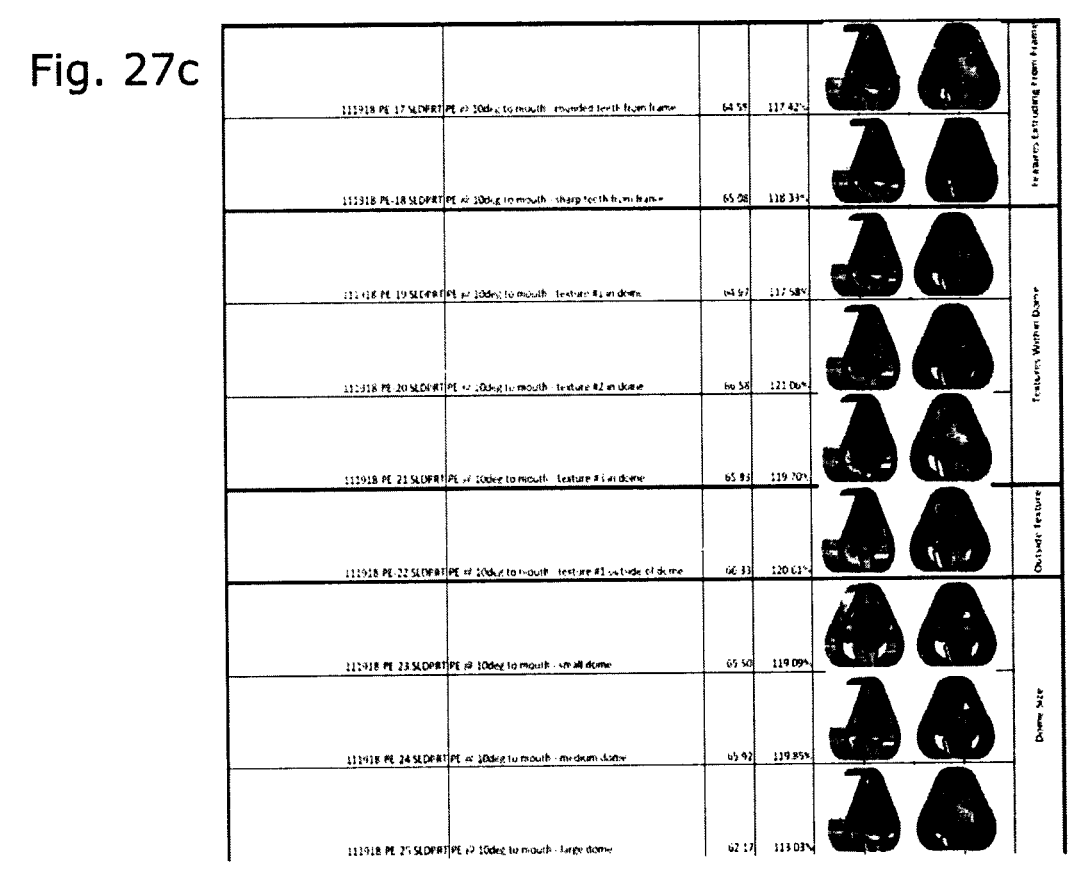

FIGS. 27A-C provide a table showing test data for various examples and a control. The table shows gas flow rates that were achieved with a control mask consisting of Southmedic™ Oxymask™ model number OM1125-8. The tests were performed on a simulated patient consisting of a mannequin head having oral and nasal passageways, connected to a mechanical ventilation pump for controlling total patient breath volume, breath rate and I:E ratio. A mask was mounted on the patient head, having a receptacle 20 for receiving a gas flow disrupter 30. Various configurations of flow disrupters were installed in the mask for test runs. The mask was connected to a ventilation pump for oxygen delivery to the mask. An $FiO_2$ pick-up was installed within the region of the dummy's trachea and was connected to a gas monitoring device to measure oxygen content of gas flowing through the dummy, representing gas "breathed" in through the nostrils and mouth of the dummy, whereby a higher oxygen content represents a higher efficiency of the mask at delivering oxygen to the patient. Oxygen was delivered to the mask at a flow rate of 10 lpm. The effectiveness of the different flow disrupter configurations was determined by taking an average of multiple $FiO_2$ readings for each tested configuration.

The $FiO_2$ results generated in this test, for the control and inventive examples, are shown in the table of FIGS. 27A-C.

While this invention has been particularly shown and described with reference to exemplary embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Moreover, any combination of the above-described elements in all possible variations thereof is encompassed by the invention unless otherwise indicated herein or otherwise clearly contradicted by context.

The invention claimed is:

1. A mask for administering a breathable gas to a patient, the mask comprising a mask body and a gas flow disrupter joined to the mask body, the mask body configured to position the flow disrupter in a position spaced from and opposing the patient's nose and mouth region when worn by the patient, and a gas inlet within the mask body for discharging gas from a source into an interior of the mask body through the flow disrupter, the flow disrupter comprising:
    a peripheral wall that defines an interior space within the periphery of the wall, the wall having an inside surface facing the interior space and an outside surface;
    a baffle structure located within the interior space, the baffle structure comprising a baffle member configured to block a portion of the interior space within the flow disrupter, the baffle structure further comprising at least one gas turbulence generator consisting of one or more of a rib, a fin, a dimple, a protuberance;
    at least one gap between the baffle member and the inside surface of the peripheral wall for gas flow through the flow disrupter.

2. The mask of claim 1, wherein the baffle member comprises a dome.

3. The mask of claim 2, wherein the dome has a concave surface facing the inlet in the path of the gas discharged from the inlet.

4. The mask of claim 1, wherein the gas turbulence generator comprises at least one fin that is aligned with an axis that is angled relative to the direction of airflow through the flow disrupter.

5. The mask of claim 1, wherein the gas turbulence generator comprises at least one fin that spans said gap.

6. The mask of claim 1, wherein said baffle member comprises a peripheral rim that joins with the inside surface of the wall along a portion of said rim.

7. The mask of claim 1, wherein the baffle member is configured to block between about 50% and 90% of the flow disrupter.

8. The mask of claim 1, further comprising a sampler for sampling exhaled breath.

9. The mask of claim 8, wherein in the sampler comprises a tube having an inlet opening within the baffle structure.

10. The mask of claim 8, wherein the baffle member comprises a dome, wherein the dome has a concave surface facing the patient's nose and mouth.

11. The mask of claim 1, wherein the gas turbulence generator comprises an array of fins that radiate from the baffle member, at least one of the fins being angled relative to a radius of the baffle member.

12. The mask of claim 11, wherein the fins are arranged in a configuration comprising one or more of parallel pair fins, converging paired fins or equally spaced fins.

13. The mask of claim 1, wherein the inside surface of the peripheral wall comprises at least one protuberance that extends inwardly towards the baffle structure with a gap between the at least one protuberance and the baffle structure.

14. The mask of claim 13, wherein the at least one protuberance consists of one or more of a rib, a ridge or a fin.

15. The mask of claim 1, wherein the baffle member is positioned within the flow disrupter whereby the baffle member is centrally disposed within the peripheral wall whereby the at least one gap between the peripheral wall and the baffle member have generally equal areas, or upwardly displaced within the peripheral wall whereby the at least one gap between the peripheral wall and the baffle member have a greater area below the baffle member compared to above the baffle member, or downwardly displaced within the peripheral wall whereby the at least one gap between the baffle member and the peripheral wall have a greater area above the baffle member compared to below the baffle member.

16. The mask of claim 1, wherein the baffle member has a opposing surfaces whereby one or both of said surfaces have gas flow disrupting structures consisting of one or more of protrusions or recesses.

17. The mask of claim 16, wherein the protrusions consist of one or more of ridges, ribs, swirls, or bumps.

18. The mask of claim 16, wherein the recesses consist of dimples.

19. The mask of claim 1, wherein the peripheral wall has an inside rim facing the patient, the rim comprising flow disrupting structures consisting of one or more protrusions or recesses.

20. The mask of claim 1, wherein the gas flow disrupter and mask body comprise mechanically interlocking structures.

21. The mask of claim 20, wherein the mechanical interlocking structures comprise at least one flexible prong and a recess configured to receive the prong for snap-lock engagement.

* * * * *